US 12,048,800 B2

United States Patent
McGuckin et al.

(10) Patent No.: US 12,048,800 B2
(45) Date of Patent: Jul. 30, 2024

(54) PORTABLE INHALATION THERAPEUTIC AND INHALATION AND EXHALATION MEASURING DEVICES AND RELATED METHODS

(71) Applicant: Argospire Medical Inc., Philadelphia, PA (US)

(72) Inventors: Terrence McGuckin, Philadelphia, PA (US); Kirsten Collier, Philadelphia, PA (US); Ashmit Gupta, Philadelphia, PA (US)

(73) Assignee: Argospire Medical Inc., Philadelphia, PA (US)

( * ) Notice: Subject to any disclaimer, the term of this patent is extended or adjusted under 35 U.S.C. 154(b) by 324 days.

(21) Appl. No.: 17/208,442

(22) Filed: Mar. 22, 2021

(65) Prior Publication Data

US 2021/0379300 A1    Dec. 9, 2021

Related U.S. Application Data

(63) Continuation of application No. 16/613,542, filed as application No. PCT/US2019/020716 on Mar. 5, 2019, now Pat. No. 10,953,164.

(Continued)

(51) Int. Cl.
*A61M 11/00* (2006.01)
*G16H 20/13* (2018.01)

(52) U.S. Cl.
CPC ............ *A61M 11/005* (2013.01); *G16H 20/13* (2018.01); *A61M 2205/0294* (2013.01);
(Continued)

(58) Field of Classification Search
CPC ....... A61B 5/087; A61B 5/0205; A61B 5/081; A61M 11/05; A61M 11/007; A61M 15/0021
See application file for complete search history.

(56) References Cited

U.S. PATENT DOCUMENTS

| 5,277,196 A | 1/1994 | Hankinson et al. |
| 8,714,150 B2 | 5/2014 | Alelov |

(Continued)

FOREIGN PATENT DOCUMENTS

| GB | 2 524 779 A | 10/2015 |
| JP | 08-506746 A | 7/1996 |

(Continued)

OTHER PUBLICATIONS

Office Action on JP Appl. No. 2020-570405 dated Jan. 17, 2023.
(Continued)

*Primary Examiner* — Margaret M Luarca
(74) *Attorney, Agent, or Firm* — Foley & Lardner LLP

(57) ABSTRACT

A portable inhalation device includes a medication storage component, a flow controller, an atomizer, a medication delivery component, and a pressure sensor. The medication storage component is configured to store medication. The flow controller is configured to cause a force to be applied to the medication stored by the medication storage component to transport the medication to the atomizer. The atomizer is configured to generate droplets from the medication. The medication delivery component includes a delivery channel extending from the atomizer to an outlet opening. The medication delivery component is configured to receive the medication in the delivery channel from the atomizer and dispense the medication via the opening. The pressure sensor is configured to detect a pressure corresponding to a flow rate of air in the delivery channel and output an indication of the detected pressure.

19 Claims, 15 Drawing Sheets

Related U.S. Application Data

(60) Provisional application No. 62/638,658, filed on Mar. 5, 2018.

(52) U.S. Cl.
CPC .............. *A61M 2205/3334* (2013.01); *A61M 2205/3344* (2013.01); *A61M 2205/50* (2013.01); *A61M 2230/46* (2013.01)

(56) References Cited

U.S. PATENT DOCUMENTS

| | | |
|---|---|---|
| 2002/0023639 A1 | 2/2002 | Ivri et al. |
| 2005/0087189 A1 | 4/2005 | Crockford et al. |
| 2009/0151718 A1* | 6/2009 | Hunter .................. A61B 5/087 |
| | | 600/538 |
| 2011/0048415 A1 | 3/2011 | Zierenberg et al. |
| 2015/0112707 A1 | 4/2015 | Manice et al. |
| 2015/0165137 A1 | 6/2015 | Mullinger et al. |
| 2015/0273165 A1 | 10/2015 | Hadash |
| 2015/0283339 A1 | 10/2015 | Mahadevan et al. |
| 2016/0325058 A1* | 11/2016 | Samson ............... A61B 5/0022 |
| 2017/0119981 A1 | 5/2017 | Davidson et al. |
| 2017/0290527 A1* | 10/2017 | Morrison .......... A61M 16/0051 |
| 2019/0254534 A1* | 8/2019 | Koltowski ............. A61B 5/087 |

FOREIGN PATENT DOCUMENTS

| | | |
|---|---|---|
| JP | 2017-515614 A | 6/2017 |
| JP | 2017-536207 A | 12/2017 |
| WO | WO-01/58514 A1 | 8/2001 |
| WO | WO-2015/109259 A1 | 7/2015 |
| WO | WO-2016/041576 A1 | 3/2016 |

OTHER PUBLICATIONS

International Preliminary Report on Patentability on International Appl. No. PCT/US2019/020716, dated Sep. 17, 2020.
International Search Report and Written Opinion for PCT Appl. No. PCT/US2019/020716, mailed Jun. 6, 2019.
Non-Final Office Action on U.S. Appl. No. 16/613,542 dated May 21, 2020.
Notice of Allowance on U.S. Appl. No. 16/613,542 dated Oct. 1, 2020.
Extended EP Search Report on EP appl. No. 19763677.2 dated Mar. 26, 2021.
First Office Action and Search Report on CN Appl. No. 2019800297108 dated Feb. 8, 2022.
Notice of Allowance for CN Appl. No. 2019800297108, dated Jul. 27, 2022.
Second Search Report on CN Appl. No. 2019800297108, dated Jul. 27, 2022.
Extended European Search Report for EP Appl. No. 22181692.9, dated Sep. 21, 2022 (9 pages).
Office Action on JP Appl. No. 2023-129949 dated Mar. 19, 2024.

* cited by examiner

PORTABLE INHALATION THERAPEUTIC AND INHALATION AND EXHALATION MEASURING DEVICES AND RELATED METHODS

CROSS-REFERENCE TO RELATED APPLICATIONS

The present application claims the benefit of and priority to U.S. Provisional Application No. 62/638,658, titled "PORTABLE INHALATION THERAPEUTIC AND INHALATION AND EXHALATION MEASURING DEVICES AND RELATED METHODS," filed Mar. 5, 2018, the disclosure of which is incorporated herein by reference in its entirety.

TECHNICAL FIELD

The present disclosure relates generally to the field of inhalation devices, and more specifically to apparatuses, systems, and methods relating to portable inhalation therapeutic and inhalation and exhalation measuring devices.

BACKGROUND

Nebulizing devices, such as inhalers, can be used to deliver therapeutic medication to a patient by inhalation. In existing devices, medication delivery may occur by manual actuation of a medication source, which may limit the ability of the device to deliver medication in a dosage targeted to the patient and the condition of the patient. Similarly, the patient may be unaware of the severity of their condition, so that even if the device is capable of dosage control, the device may be limited in effectively delivering the medication with an appropriate dosage, and the device may be incapable of providing the patient with an indication of the severity of their condition. While some existing systems implement a surface tension- or gravity-based mechanism for delivering medication, these systems are often limited in functionality because they can only be used in a single orientation (e.g., upright orientation).

SUMMARY

According to an aspect of the present disclosure, a portable inhalation device includes a medication storage component, a flow controller, an atomizer, a medication delivery component, and a pressure sensor. The medication storage component is configured to store medication. The flow controller is configured to cause a force to be applied to the medication stored by the medication storage component to transport the medication to the atomizer. The atomizer is configured to generate droplets from the medication. The medication delivery component includes a delivery channel extending from the atomizer to an outlet opening. The medication delivery component is configured to receive the medication in the delivery channel from the atomizer and dispense the medication via the opening. The pressure sensor is configured to detect a pressure corresponding to a flow rate of air in the delivery channel and output an indication of the detected pressure.

In some embodiments, the portable inhalation device is configured to collect and/or track airway measurement data before, during and/or after treatment. In some embodiments, the portable inhalation device can include a communication module, such as Bluetooth, that is configured to receive airway measurement data before, during, and after treatment.

In some embodiments, the portable inhalation device can include an integrated pulse oximeter to collect blood oxygen levels. The integrated pulse oximeter can be sized and configured on the portable inhalation device such that the pulse oximeter can determine a blood oxygen level of a user while the user is holding the portable inhalation device. The portable inhalation device can be configured to collect both the airway measurement data with blood oxygen levels to determine a correlation between a status of an airway and blood oxygen levels. In some embodiments, the portable inhalation device can be configured to receive or obtain measurements throughout the day and these measurements will be linked to other specific variables at that moment in time such as geographic location (urban vs rural), allergy maps, air quality, pollen counts, and weather. In some embodiments, the portable inhalation device can include a location sensor, such as a GPS, to determine a current location of the portable inhalation device. Using the location obtained from the location sensor, values for specific variables for that location can be determined. The storage of this data over time will provide valuable predictive insight into the individual's asthma state (e.g., the asthma is worse during times when the pollen counts are over a certain level or the humidity is over a certain percentage). The data can be evaluated with specific proprietary algorithms and calculations. This information can provide actionable information that allows for informed health care decisions by their health care provider.

In some embodiments, the portable inhalation device can include a removable cartridge that stores medication. The portable inhalation device can include a fluid pathway from a location proximal to where the removable cartridge is inserted within the portable inhalation device and the piezoelectric device. With the use of a cartridge, there is less of a barrier to use and improved compliance as it is easier and less effort to start the nebulization process. The cartridge housing will have tactile haptic feedback on placement and removal to further simplify the experience.

According to an aspect of the present disclosure, a portable inhalation device includes a nozzle, an atomizer, a medication cartridge, a flow controller, and a processing circuit. The nozzle defines a delivery channel coupled with an outlet and at least one vent. The atomizer is adjacent to the delivery channel, and configured to receive a medication and generate droplets from the medication to output the generated droplets from the outlet of the nozzle. The medication cartridge is configured to store the medication, and is coupled with the atomizer via a medication channel. The flow controller is configured to cause a force to be applied to the medication in the medication cartridge to drive the medication from the medication cartridge to the atomizer. The processing circuit is configured to control operation of the flow controller responsive to a trigger condition being satisfied.

According to an aspect of the present disclosure, a method of operating a portable inhalation device includes detecting, by a pressure sensor, a pressure associated with a delivery channel, the delivery channel defined by a nozzle and coupled with an outlet and at least one vent, determining, by one or more processors, that the pressure satisfies a trigger condition, causing, by the one or more processors, a flow controller to cause a force to be applied to medication stored in a medication cartridge to drive the medication from the medication cartridge though a medication channel to an atomizer adjacent to the delivery channel, generating, by the atomizer, droplets from the medication, and outputting the droplets from the outlet via the delivery channel.

According to an aspect of the present disclosure, a portable inhalation device includes a nozzle, a pressure sensor, a piezoelectric atomizer, a medication cartridge, a flow controller, and a processing circuit. The nozzle defines a delivery channel coupled with an outlet, a sensor opening, and at least one vent. The pressure sensor is coupled with the sensor opening, and configured to detect a pressure of the delivery channel. The atomizer is adjacent to the delivery channel, and configured to receive a medication and generate droplets from the medication to output the generated droplets from the outlet of the nozzle. The medication cartridge is configured to store the medication, and is coupled with the atomizer via a medication channel. The flow controller is configured to cause a force to be applied to the medication in the medication cartridge to drive the medication from the medication cartridge to the atomizer. The processing circuit is configured to control operation of the atomizer and the flow controller responsive to a trigger condition being satisfied, the trigger condition based on at least one of the pressure detected by the pressure sensor or a user input.

DETAILED DESCRIPTION

Figure 1:
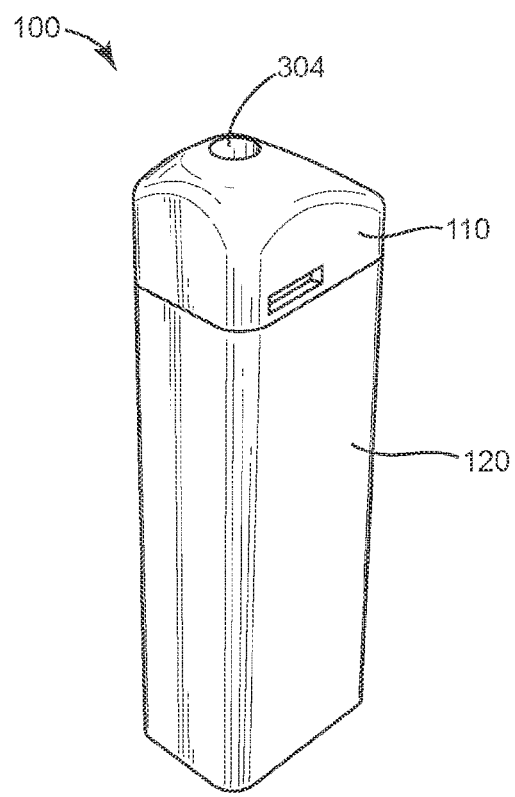
FIG. 1 illustrates a perspective view of an embodiment of a portable inhalation device according to an embodiment of the present disclosure.

The following detailed description and the appended drawings describe and illustrate various fluid control systems, methods, and components. The description and drawings are provided to enable one of skill in the art to make and use one or more fluid control systems and/or components, and/or practice one or more methods. They are not intended to limit the scope of the claims in any manner.

The use of "e.g." "etc.," "for instance," "in example," and "or" and grammatically related terms indicates non-exclusive alternatives without limitation, unless otherwise noted. The use of "optionally" and grammatically related terms means that the subsequently described element, event, feature, or circumstance may or may not be present/occur, and that the description includes instances where said element, event, feature, or circumstance occurs and instances where it does not. The use of "attached" and "coupled" and grammatically related terms refers to the fixed, releasable, or integrated association of two or more elements and/or devices with or without one or more other elements in between. Thus, the term "attached" or "coupled" and grammatically related terms include releasably attaching or fixedly attaching two or more elements and/or devices in the presence or absence of one or more other elements in between. As used herein, the terms "proximal" and "distal" are used to describe opposing axial ends of the particular elements or features being described in relation to anatomical placement.

In existing solutions for portable inhalation devices, it is typically difficult to both provide medication doses specific to a patient and a current condition of the patient, and also measure characteristics of inhalation and exhalation by the patient to determine the quality of breathing by the patient (e.g., determine how well the lungs are working). Existing solutions also typically require portable inhalation devices to be used in limited orientations, such as by only functioning properly when held upright to enable gravity feeding of the medication to a mouthpiece. The present solution provides systems, methods, and apparatuses for improving medication delivery and exhalation measurement in portable inhalation devices by enabling precise dosing and exhalation measurement, as well as enabling the devices to be used in any orientation. In some embodiments, a portable inhalation device includes a medication storage component, a flow controller, an atomizer, a medication delivery component, and a pressure sensor. The medication storage component is configured to store medication. The flow controller is configured to cause a force to be applied to the medication stored by the medication storage component to transport the medication to the atomizer. The atomizer is configured to generate droplets from the medication. The medication delivery component includes a delivery channel extending from the atomizer to an outlet opening. The medication delivery component is configured to receive the medication in the delivery channel from the atomizer and dispense the medication via the opening. The pressure sensor is configured to detect a pressure corresponding to a flow rate of air in the delivery channel and output an indication of the detected pressure.

Referring to FIG. 1, a portable inhalation device 100 is shown according to an embodiment of the present disclosure. The portable inhalation device 100 includes a medication delivery component 110 and a body 120. The medication delivery component 110 defines an outlet opening 304 through which the medication delivery component 110 can deliver medication (e.g., deliver medication stored in the body 120).

Figure 2A:
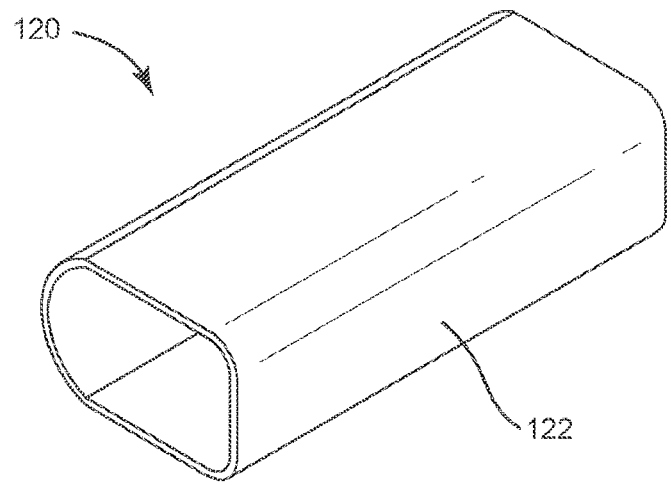
FIGS. 2A and 2B illustrate a perspective view of a body and interior assembly, respectively, of the portable inhalation device of FIG. 1 according to an embodiment of the present disclosure.
Figure 2B:
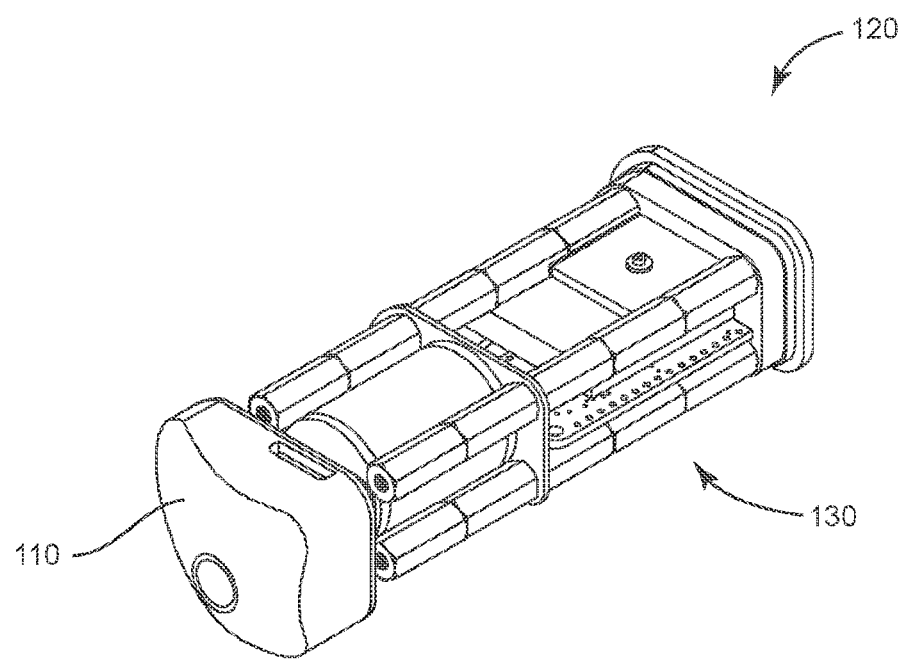

Referring to FIGS. 2A-2B, the body 120 and an interior assembly 130 of the portable inhalation device 100 are shown according to an embodiment of the present disclosure. The body 120 includes a cover member 122 configured to cover the interior assembly 130. The cover member 122 can be configured to be gripped by the hand of the user. In some embodiments, the cover member 122 is removably coupled to at least one of the interior assembly 130 or the medication delivery component 110. For example, the cover member 122 can be removed from the portable inhalation device 100 to enable access to a medication storage component (e.g., medication storage component 150, see FIG. 3).

Figure 3:
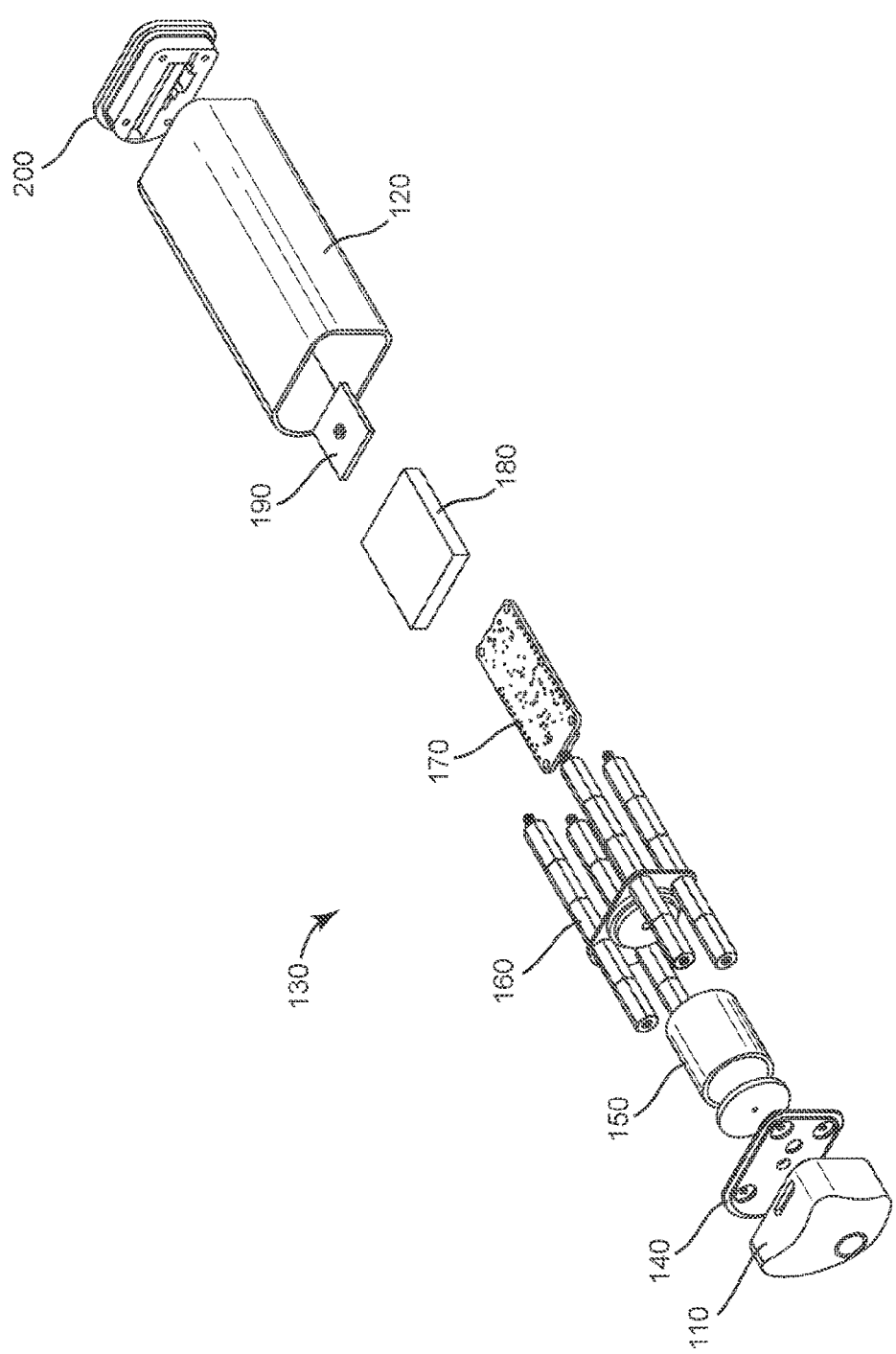
FIG. 3 illustrates an exploded view of the portable inhalation device of FIG. 1 according to an embodiment of the present disclosure.

Referring to FIG. 3, an exploded view of the portable inhalation device 100 is shown according to an embodiment of the present disclosure. In some embodiments, the portable inhalation device 100 includes a plate 140. The plate 140 can be configured to be attached to a side of the medication delivery component 110 opposite the outlet opening 304.

In some embodiments, the portable inhalation device 10) includes a medication storage component 150. The medication storage component 150 can include a container (e.g., bottle) storing a medication. The medication storage component 150 can be made of glass, plastic, metal (e.g., stainless steel), a composite material, or any other material compatible with medication for atomization or nebulization. The medication storage component 150 can have a cylindrical shape. The medication can be an asthma medication, such as albuterol, or any other medication used with a nebulizer.

In some embodiments, the portable inhalation device 100 includes a support structure 160. The support structure 160 can be configured to support (e.g., hold) the medication storage component 150 in place within the portable inhalation device 100 (e.g., secure the medication storage component 150 relative to medication delivery component 110 and flow controller 190). The medication storage component 150 can be removably coupled to the support structure 160. The support structure 160 can be removably coupled to the plate 140 and/or the medication delivery component 110.

The portable inhalation device 100 can include a processing circuit 170. The processing circuit 170 can include a processing circuit including a processor and memory. The processor may be implemented as a specific purpose processor, an application specific integrated circuit (ASIC), one or more field programmable gate arrays (FPGAs), a group of processing components, or other suitable electronic processing components. The memory is one or more devices (e.g., RAM, ROM, flash memory, hard disk storage) for storing data and computer code for completing and facilitating the various user or client processes, layers, and modules described in the present disclosure. The memory may be or include volatile memory or non-volatile memory and may include database components, object code components, script components, or any other type of information structure for supporting the various activities and information structures of the inventive concepts disclosed herein. The memory is communicably connected to the processor and includes computer code or instruction modules for executing one or more processes described herein. The memory can include various circuits, software engines, and/or modules that cause the processor to execute the systems and methods described herein.

As shown in FIG. 3, the processing circuit 170 is implemented using a circuit board. The circuit board may also include communications electronics, such as a Bluetooth antenna and/or a WiFi antenna. The portable inhalation device 100 can be configured to receive and transmit signals from/to an electronic device, such as a portable electronic communication device, such as a cell phone. For example, the portable inhalation device 100 can receive patient dosage information from the electronic device, and transmit inhalation or exhalation data (e.g., spirometry data) to the electronic device. The portable inhalation device 100 can include a power source 180. In some embodiments, the power source 180 includes a battery. The power source 180 can be a rechargeable battery. The power source 180 can be configured to output electrical power (e.g., a voltage, current or other electrical waveform) sufficient to actuate operation of mechanical and electrical components of the portable inhalation device 100, including the processing circuit 170, flow controller 190, and/or an atomizer (e.g., atomizer 340 as shown in FIG. 3). For example, the power source 180 can include or be coupled to drive electronics (e.g., a driver) that can convert voltages outputted by the power source 180 to voltages used to operate the flow controller 190 and atomizer 340, which may include voltages from −50V to 50V (which may be boosted to a higher voltage peak to peak, such as 75V); DC voltages; periodic voltages with a range of frequencies and duty cycles. In some embodiments, the power source 180 is configured to output a voltage greater than or equal to 3V and less than or equal to 5V (e.g., 3.7 V; multiples of voltages greater than or equal to 3V and less than or equal to 5V in a multiple cell configuration). The power source 180 can have a capacity sufficient to actuate operation of mechanical and electrical components of the portable inhalation device 100 for a threshold number of use cycles (e.g., at least ten use cycles; at least fifty use cycles). In some embodiments, the power source 180 has a capacity greater than or equal to 200 mAh and less than or equal to 1000 mAh (e.g., 500 mAh).

The portable inhalation device 100 can include a flow controller 190. The flow controller 190 is configured to cause a force to be applied on the medication stored in the medication storage component 150, which can transport the medication to an atomizer (e.g., atomizer 340) for delivery via the medication delivery component 110. In some embodiments, the flow controller 190 includes a microblower, such as a piezoelectric diaphragm, configured to drive air flow for applying pressure on the medication. In some embodiments, the flow controller 190 includes a check valve to prevent liquid from flowing (backwards) from the medication storage component 150 to the flow controller 190.

The portable inhalation device 100 can include a removable end cap 200. The removable end cap 200 may be removed to provide access into the cover member 122, such as for accessing or retrieving the power source 180 for recharging or replacement.

Figure 4:
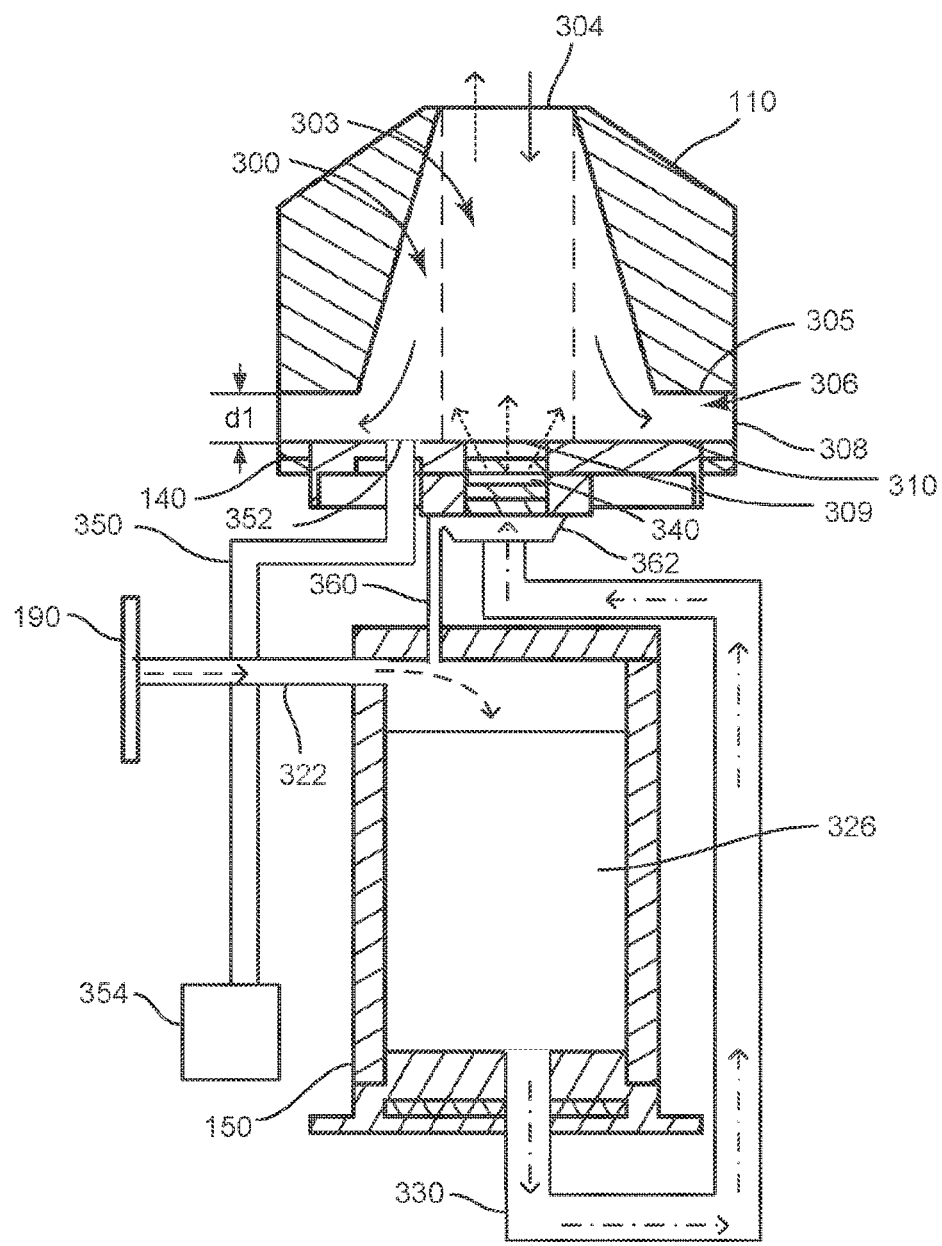
FIG. 4 illustrates a detail section view of a medication delivery assembly of the portable inhalation device of FIG. 1 according to an embodiment of the present disclosure.

Referring to FIG. 4, a section view of the portable inhalation device 100 illustrating therapeutic medication delivery and measurement operations performed by the portable inhalation device 100 is shown according to an embodiment of the present disclosure. The medication delivery component 110 can be configured as a nozzle for dispensing medication. The medication delivery component 110 can be configured as a mouthpiece, such as for a user to exhale into or inhale from the medication delivery component 110. In some embodiments, the medication delivery component 110 defines a delivery channel 300. The delivery channel 300 includes a first flow path 303 (e.g., bounded by the dashed lines as shown in FIG. 4) extending in a direction perpendicular to an outlet opening 304 towards an atomizer opening 309. The medication can be dispensing from the medication delivery component 110 via the outlet opening 304.

The medication delivery component 110 includes a nozzle wall 305 defining at least a portion of the delivery channel 300 in some embodiments, a distance across the delivery channel 300 as defined by the nozzle wall 305 increases from the outlet opening 304 towards an end of the medication delivery component 110 opposite the outlet opening 304 (e.g., towards atomizer opening 309). As such, a cross sectional area of the delivery channel 300 increases in a direction away from the outlet opening 304, resulting in a decrease in pressure from the outlet opening 304 towards the atomizer opening 309. In some embodiments, the decrease in pressure from the outlet opening 304 towards the atomizer opening 309 may improve accuracy of a pressure detected by pressure sensor 354.

In some embodiments, the delivery channel 300 includes side channels 306 extending to one or more side openings 308 (e.g., vents). The side openings 308 can allow air to enter the delivery channel 300 while air is dispensed from the outlet opening 304 (e.g., during inhalation) or vice versa. As shown by the solid arrows in FIG. 4, when air enters the delivery channel 300 via outlet opening 304, the air can pass through the delivery channel 300 and out of side channels 306. In some embodiments, the side openings 308 improve the usability of the portable inhalation device 100 by allowing air to flow through the delivery channel 300, rather than merely being pushed into or pulled out of the delivery channel 300 (e.g., if the delivery channel 300 only had one opening at the outlet opening 304). The flow-through of air can also improve operation of the pressure sensor 354, which may be configured to provide more accurate pressure values based on air flowing past sensor opening 352 as compared to air being pushed into or pulled out of sensor opening 352 due to the range of pressures resulting from flow-through of air matching pressures for which the pressure sensor 354 is calibrated.

In some embodiments, the portable inhalation device 100 is configured to cause laminar flow in the side channels 306. For example, a distance d1 between the nozzle wall 305 and an end wall 310 defining the atomizer opening 309 can be configured to cause laminar flow in the side channels 306 at expected operating conditions (e.g., temperature between approximately −50 degrees Fahrenheit and 120 degrees Fahrenheit; air flow rates corresponding to typical human inhalation or exhalation flow rates). A shape of the nozzle wall 305 (e.g., angle of bends or changes in shape) can be configured to cause laminar flow.

The medication storage component 150 is configured to store medication 326. The medication 326 can be in a liquid form. The medication storage component 150 can be configured to receive a force from the flow controller 190. For example, the flow controller 190 can apply pressure on air (indicated by dashed arrow) in a flow channel 322, driving the air to apply pressure on the medication 326. In some embodiments, the flow controller 190 is configured to apply an output pressure on the air greater than a threshold pressure sufficient to drive medication 326 to atomizer 340 in any orientation (e.g., regardless of a direction of gravity).

The medication 326 can flow (as shown by dot-dash arrows) through a medication channel 330 to the atomizer 340. While flowing through the medication channel 330, the medication 326 may be in a liquid state (e.g., continuous state, the medication does not form droplets in the medication channel 330; the medication forms large drops having a size magnitude on a similar order as dimensions of the medication channel 330), or has a droplet size (e.g. average droplet size) greater than a first size threshold. In some embodiments, the first size threshold is greater than 1 millimeter. The medication channel 330 can have a diameter greater than a threshold diameter at which flow of medication 326 as driven by the flow controller 190 would be too restricted to provide a dosage of medication 326 within a predetermined period of time.

The atomizer 340 is configured to generate droplets (e.g., a dispersed mist of droplets) from the medication 326 (as shown by small dashed arrows in the delivery channel 300) For example, the atomizer 340 can generate droplets from the medication 326 that have a droplet size less than a second size threshold, where the second size threshold is less than or equal to the first size threshold. In some embodiments, the second size threshold is greater than 10 nanometers and less than 100 micrometers. The atomizer 340 can include a nebulizer. The atomizer 340 can be configured to increase a velocity of the medication 326 in a direction towards the outlet opening 304. In some embodiments, the atomizer 340 includes a piezoelectric element configured to generate droplets from the medication 326. The piezoelectric element can cause a vibrating mesh to vibrate to generate the droplets. The vibrating mesh can have micro-holes sized on the orders of approximately 1 micron to 10 microns, such that oscillation of the vibration mesh generates the droplets from the medication 326.

The processing circuit 170 can control operation of the flow controller 190. In some embodiments, the processing circuit 170 can control a dosage of medication 326 delivered by the portable inhalation device 100 by controlling operation of the flow controller 190. For example, the processing circuit 170 can include a dosage database mapping a duration of action of flow controller 190 to dosage values. The flow controller 190 may be configured to apply a predetermined pressure based on a control signal received from the processing circuit 170. The processing circuit 170 can receive or determine a dosage value, retrieve a corresponding duration of operation from the dosage database, generate a flow signal indicating the duration of operation, and transmit the flow signal to the flow controller 190 to cause the flow controller 190 to operate for the selected duration. It will be appreciated that a dosage dispensed by the portable inhalation device 100 may be a function of the pressure applied by the flow controller 190 and a duration for which the pressure is applied by the flow controller 190. The processing circuit 170 may additionally or alternatively be configured to control a pressure outputted by the flow controller 190 to cause the desired dosage to be dispensed from the portable inhalation device 100.

The processing circuit 170 can control operation of the atomizer 340. For example, the processing circuit 170 can transmit a control signal to the atomizer 340 to cause the atomizer 340 to operate (e.g., generate droplets from the medication 326 and/or increase the velocity of the medication in a direction towards the outlet opening 304). In some embodiments, the processing circuit 170 is configured to cause the atomizer 340 to operate for a predetermined period of time corresponding to operation of the flow controller 190. For example, the processing circuit 170 can initiate operation of the flow controller 190 at a first point in time, and initiate operation of the atomizer 340 at a second point in time no later than a first time delay subsequent to the first point in time. As such, the processing circuit 170 can ensure that the atomizer 340 is operating when medication 326 has been driven from the medication storage component 150 to the atomizer 340 through the medication channel 330 by the flow controller 190 in some embodiments, the first time delay corresponds to a period of time required for medication 326 to flow from the medication storage component 150 to the atomizer 340. The processing circuit 170 can terminate operation of the atomizer 340 at a third point in time subsequent to the first point in time by a second time delay. The second time delay may correspond to a duration of time required by the atomizer 340 to generate droplets from the medication 326 of the desired dosage. In various embodiments, by controlling timing of operation of the flow controller 190 and the atomizer 340, the processing circuit 170 can cause the portable inhalation device 100 to dispense precise medication dosages. At least one of the first time delay or the second time delay can correspond to a function of at least one of: (1) output pressure of the flow controller 190; (2) distance in the medication channel 330 from the medication storage component 150 to the atomizer 340; and (3) rate of atomization of the atomizer 340 (e.g., rate of dispensation of medication by the atomizer 340).

The portable inhalation device 100 includes a pressure sensor 354. The pressure sensor 354 is fluidly coupled to the side channel 306 via a sensor opening 352 in a sensor channel 350. As shown in FIG. 4, the sensor opening 352 can be located outside of the first flow path 303 of the delivery channel 300. In some embodiments, the location of the sensor opening 352 improves the accuracy of the pressure detected by the pressure sensor 354, such as by reducing cross flow or turbulent effects from air flow in the first flow path 303 (e.g., due to inhalation or exhalation) The sensor opening 352 can be located flush with the end wall 310, which may reduce turbulence at the sensor opening 352. The pressure sensor 354 can be a differential pressure sensor. The pressure sensor 354 can be a MEMS (microelectromechanical system) device. In some embodiments, the pressure sensor 354 is configured to output a pressure signal indicating the pressure at the sensor opening 352 (e.g., a voltage corresponding to the pressure at the sensor opening 352). The pressure detected by the pressure sensor 354 can indicate a flow rate of air in the delivery channel 300, such that the flow rate may be determined based on the pressure.

The portable inhalation device 100 can include an overspill channel 360. The overspill channel 360 can fluidly couple the atomizer 340 to the medication storage component 150. In some embodiments, the overspill channel 360 includes an overspill chamber 362 disposed adjacent to the atomizer 340, which can receive medication 326 which is not dispensed through the atomizer 340 into the delivery channel 300. The overspill channel 360 can be separate from the medication channel 330, so that unused medication flows by the atomizer 340 before flowing into the overspill channel 360 via the overspill chamber 362. In some embodiments, by fluidly coupling the atomizer 340 to the medication storage component 150 (e.g., along a separate path than the medication channel 330), the overspill channel 360 can reduce the force required to be applied by the flow controller 190 to drive the medication 326 to the atomizer 340. For example, air in the medication channel 330 adjacent to the atomizer 340 can be moved through the overspill channel 360 back into the medication storage component 150 as the medication 326 flows out of the medication storage component 150 through the medication channel 330 to the atomizer 340. In some embodiments, additionally or alternatively to the overspill chamber 362, the portable inhalation device 100 can include a check valve configured to open a flow path from the atomizer 340 through the overspill channel 360 to the medication storage component 150 when a pressure adjacent to the atomizer 340 is greater than a threshold pressure.

In some embodiments, the flow controller 190 includes a plunger attached to the medication storage component 150. The processing circuit 170 can control operation of a plunger actuator (e.g., a linear actuator) configured to drive the plunger through the medication storage component 150, which can drive medication 326 out of the medication storage component 150. The processing circuit 170 can be configured to control a dosage of medication 326 based on a distance that the plunger is driven.

In some embodiments, the processing circuit 170 can determine the pressure based on the pressure signal. For example, the processing circuit 170 can include a lookup table mapping voltage values to pressure values (e.g., based on a predetermined calibration of the pressure sensor 354), and perform a lookup to retrieve a pressure value corresponding to a voltage of the pressure signal. In some embodiments, the processing circuit 170 is configured to execute a calibration function (e.g., a function mapping voltage to pressure) to convert the voltage to the pressure value.

The processing circuit 170 can determine a flow rate of air flow in the delivery channel 300 (e.g., volume of air per unit time, such as liters per minute)_based on the determined pressure. For example, the processing circuit 170 may store a lookup table or algorithm relating pressure to flow rate (e.g., based on calibration of the portable inhalation device 100), and can be configured to determine the flow rate by at least one of retrieving the flow rate from the lookup table based on the determined pressure or executing the algorithm using the determined pressure. In some embodiments, the processing circuit 170 can determine the flow rate based on the pressure signal (e.g., using a lookup table or algorithm relating pressure signal parameters, such as voltage, to flow rate). For example, determining the flow rate directly based on the pressure signal can reduce computational resources needed to operate the processing circuit 170, and thus can reduce one or more of the size of or power used by the processing circuit 170. It will be appreciated that the calibration functions used to convert the detected pressure to flow rate may relate pressure to one or more intermediate variables associated with the flow rate (e.g., velocity), and the processing circuit 170 may be configured to retrieve the intermediate variable and calculate the flow rate based on known parameters of the portable inhalation device 100, such as dimensions of the delivery channel 300.

In some embodiments, the processing circuit 170 can determine a duration of inhalation (or exhalation) based on the pressure signal. For example, the processing circuit 170 can receive a plurality of time-sequential pressure signals (or voltage values, or flow rate values), compare each of the plurality of pressure signals to a pressure threshold, and determine the duration based on a period of time for which one or more pressure signals are greater than the pressure threshold.

In some embodiments, the processing circuit 170 is configured to execute a spirometry algorithm, such as to determine characteristic(s) of breathing of a user of the portable inhalation device. For example, the processing circuit 170 can compute a volume of air flow corresponding to at least one of inhalation or exhalation by the user using a plurality of pressure signals. In some embodiments, the processing circuit 170 is configured to detect a plurality of air flow cycles (e.g., combinations of exhalation cycles and inhalation cycles) based on the pressure signals, and compute spirometry parameters, such as a volume of air flow through the user's lungs, and/or a rate of air inhalation and/or exhalation by the user (e.g., flow speed). The processing circuit 170 can compute the spirometry parameters as an average value across one or more air flow cycles. In some embodiments, the processing circuit 170 is configured to execute an auto calibration algorithm to determine the spirometry parameters, such as by comparing historical and/or predetermined spirometry parameters to instant parameter values.

In some embodiments, the processing circuit 170 is configured to output a breathing guidance indicator. The breathing guidance indicator can be configured to direct a user to perform a breathing exercise (e.g., inhalation and/or exhalation) which can be used to detect breathing/spirometry characteristics. The portable inhalation device 100 or a remote portable electronic device may include an output device (e.g., display, audio output device, haptic feedback device, tactile feedback device), and the processing circuit 170 can transmit a control signal to the output device to cause the output device to output the breathing guidance indicator. In some embodiments, the processing circuit 170 can initiate storage and/or analysis of pressure data from the pressure sensor 354 in response to outputting the breathing guidance indicator. In some embodiments, the processing circuit 170 can output modified breathing guidance indicators in real-time based on detecting pressure data and determining whether a breathing exercise is being performed properly based on the pressure data. The processing circuit 170 can output a plurality of breathing guidance indicators to indicate instructions for performing multiple steps in a breathing exercise. As an illustrative example, the processing circuit 170 can transmit a first control signal to cause a display (e.g., an LED light or display) to output a first color to indicate instructions for a user to inhale from the portable inhalation device 100; after a first predetermined period of time (e.g., based on expiration of a timer initiated in response to outputting the first control signal), transmit a second control signal to cause the display to output a second color to indicate instructions for the user to exhale into the portable inhalation device 100, and after a second predetermined period of time, transmit a third control signal to cause the display to discontinue outputting a color to indicate instructions for the user to discontinue exhalation.

The processing circuit 170 can control operation of at least one of the flow controller 190 or the atomizer 340 based on a trigger input. In some embodiments, the processing circuit 170 receives the trigger input by detecting inhalation through the medication delivery component 110. For example, the processing circuit 170 can periodically monitor a pressure signal received from the pressure sensor 354 and compare a pressure value of the pressure signal to a trigger threshold. The trigger threshold can be calibrated to a pressure value corresponding to a minimum pressure associated with typical or expected inhalation by a user. In response to determining that the pressure value is greater than the trigger threshold, the processing circuit 170 can initiate operation of the flow controller 190 and/or the atomizer 340 to deliver a dosage of medication 326 (which may be targeted to the user).

In some embodiments, the processing circuit 170 receives the trigger signal from a user input device. For example, the portable inhalation device 100 can include a button, switch, or other user input device configured to be actuated and to transmit a user input signal in response to being actuated. In some embodiments, the processing circuit 170 receives the trigger signal from a remote device (e.g., a portable electronic device). For example, the processing circuit 170 can receive the trigger signal as a wireless transmission from the portable electronic device (which may be running an application providing a user interface for receiving a user input corresponding to the trigger signal).

The processing circuit 170 may determine a dosage of medication 326 to be delivered by the portable inhalation device 100 based on user data stored in a user database. The user database can map one or more users to dosage. The processing circuit 170 can retrieve a dosage from the user database based on a predetermined or identified user. For example, the portable inhalation device 100 may be associated with a specific user.

In some embodiments, the processing circuit 170 is configured to determine a dosage of medication 326 to be delivered by the portable inhalation device 100 based on pressure data detected by the pressure sensor 354. For example, the processing circuit 170 can use the pressure data to determine characteristics of breathing of the user (e.g., inhalation and/or exhalation characteristics, such as flow volume or flow rate), and determine a condition of the user based on the determined characteristics. The processing circuit 170 may include a condition database mapping characteristics of breathing to one or more conditions, and retrieve a condition from the condition database based on the determined characteristics. Additionally or alternatively, the processing circuit 170 can be configured to execute a condition function to determine a condition of the user based on the determined characteristics of breathing. In some embodiments, the retrieved or determined condition may indicate a dosage, or the processing circuit 170 can execute a dosage function to determine the dosage based on the determined condition (or retrieve the dosage from a dosage database mapping conditions to dosage). The processing circuit 170 can update the user data in the user database based on the pressure data (or other parameters computed using the pressure data, such as breathing/spirometry characteristics), enabling the portable inhalation device 100 to update dosage delivery across use cycles.

While computer processing operations are described herein as being executed by the processing circuit 170 of the portable inhalation device 100, it will be appreciated that various operations may be executed on a remote processing device, such as a processing circuit of a portable electronic device. For example, the portable inhalation device 100 may store a lookup table for dosage values, which may be updated in response to receiving an update data signal from the portable electronic device. The portable inhalation device 100 may be configured to transmit raw data (e.g., output from the pressure sensor 354) to the portable electronic device, while the portable electronic device computes dosage levels, breathing/spirometry characteristics, or other values requiring calculations. As such, the size and/or computing resources required for operation of the processing circuit 170 may be reduced, which can allow the size, weight, and/or complexity of the portable inhalation device 100 to be reduced.

Figure 5A:
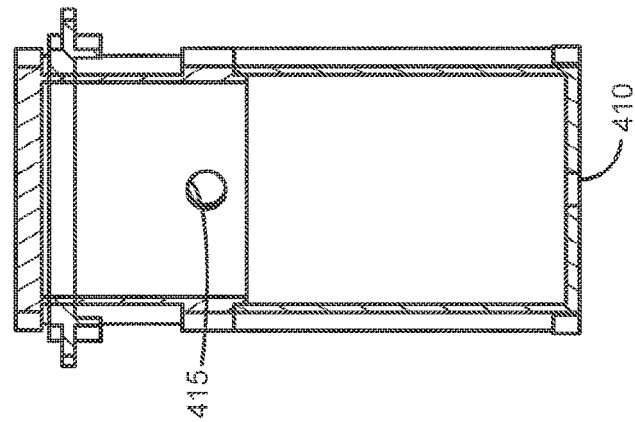
FIG. 5A illustrates a perspective view of a medication storage assembly of the portable inhalation device of FIG. 1 according to an embodiment of the present disclosure.
Figure 5B:
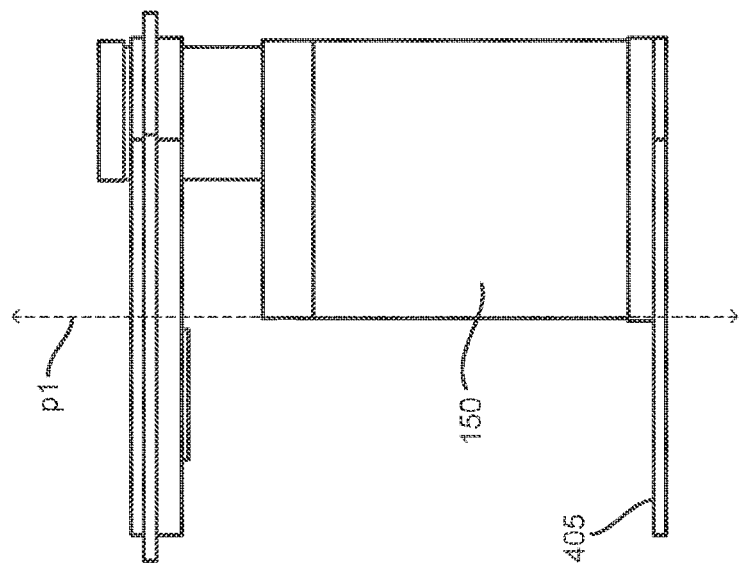
FIG. 5B illustrates aside view of the medication storage assembly of FIG. 7 according to an embodiment of the present disclosure.
Figure 5C:
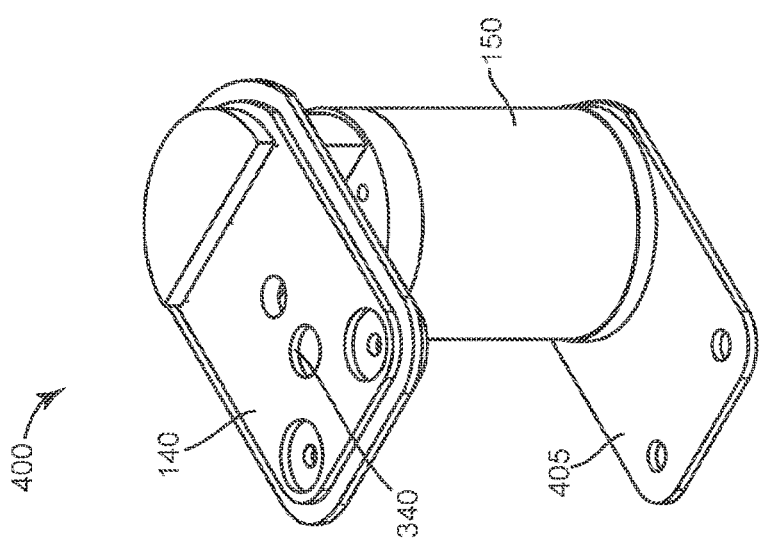
FIG. 5C illustrates a section view of the medication storage assembly of FIG. 7 according to an embodiment of the present disclosure.

Referring to FIGS. 5A-5C, a support structure 400 for the medication storage component 150 is shown according to an embodiment of the present disclosure. The support structure 400 includes the plate 140 and an outlet plate 405. The plate 140 is configured to support the atomizer 340. The outlet plate 405 can define a medication channel opening 410 configured to receive medication 326 from the medication storage component 150 for flow through the medication channel 330 (see FIG. 3). The medication storage component 150 can define an air now input opening 415 configured to receive air pressure from the flow controller 190. The plate 140 and outlet plate 405 can extend beyond a plane p1 defined by the medication storage component 150 (e.g., tangent to a side of the medication storage component 150 opposite the air flow input opening 415), which can allow for the medication channel 330 to extend to the atomizer 340 through a space adjacent to the medication storage component 150. In some embodiments, the support structure 400 is configured to be removably coupled to the support structure 160, which can facilitate adding new medication to the medication storage component 150.

Figure 6:
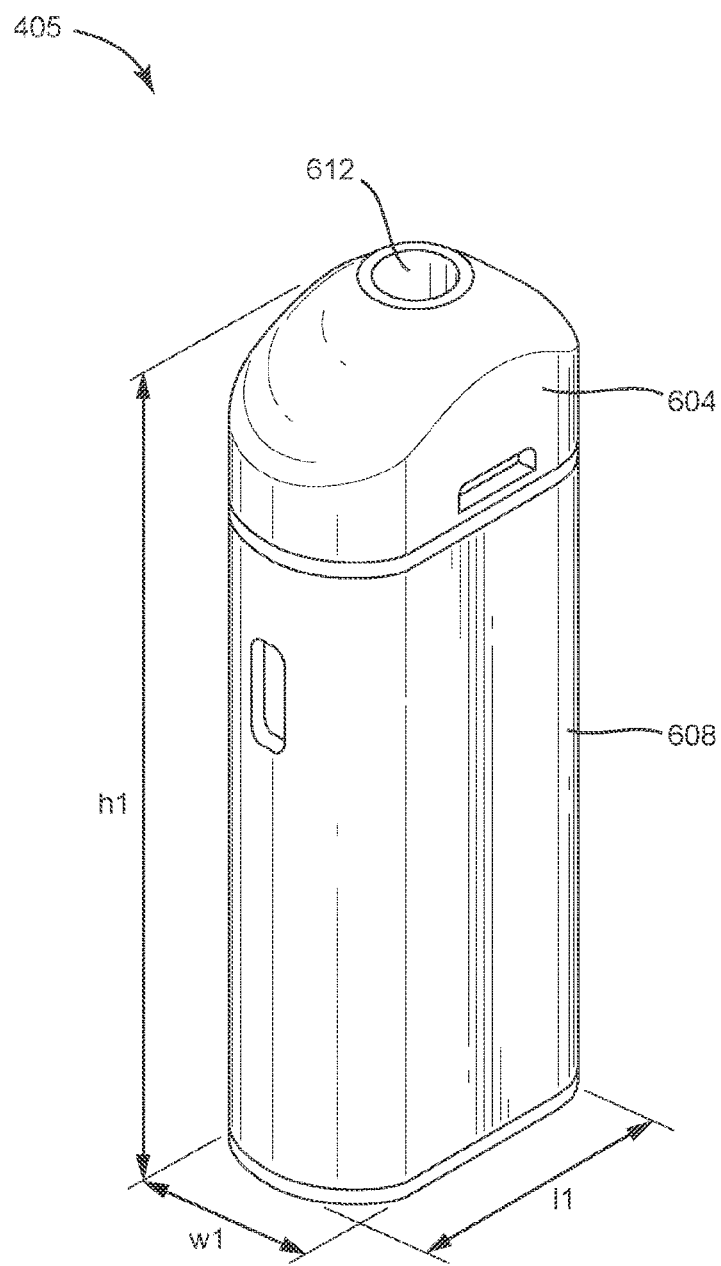
FIG. 6 is a perspective view of a portable inhalation device according to an embodiment of the present disclosure.

Referring to FIG. 6, a portable inhalation device 600 is shown according to an embodiment of the present disclosure. The portable inhalation device 600 can incorporate features of the portable inhalation device 100, and various functions described with reference to the portable inhalation device 600 can be performed by the portable inhalation device 100 and vice versa. The portable inhalation device 600 includes a medication delivery component 604 and a body 608 coupled with the medication delivery component 604. The medication delivery component 604 defines an outlet opening 612 through which the medication delivery component 604 can deliver medication (e.g., deliver medication stored in the body 608). The medication delivery component 604 can be a mouthpiece.

The portable inhalation device 600 may have a relatively small form factor, facilitating portability and ease of use. For example, the portable inhalation device 600 can define a height hi of approximately 127 mm (e.g., 127 mm; greater than or equal to 90 mm and less than or equal to 150 mm, greater than or equal to 110 mm and less than or equal to 140 mm; greater than or equal to 120 mm and less than or equal to 135 mm), a length l1 of approximately 45 mm (e.g., greater than or equal to 20 mm and less than or equal to 70 mm; greater than or equal to 30 mm and less than or equal to 60 mm; greater than or equal to 40 mm and less than or equal to 50 mm), and a width w1 of approximately 30 mm (e.g., greater than or equal to 10 mm and less than or equal to 50 mm; greater than or equal to 20 mm and less than or equal to 40 mm; greater than or equal to 25 mm and less than or equal to 35 mm).

Figure 7:
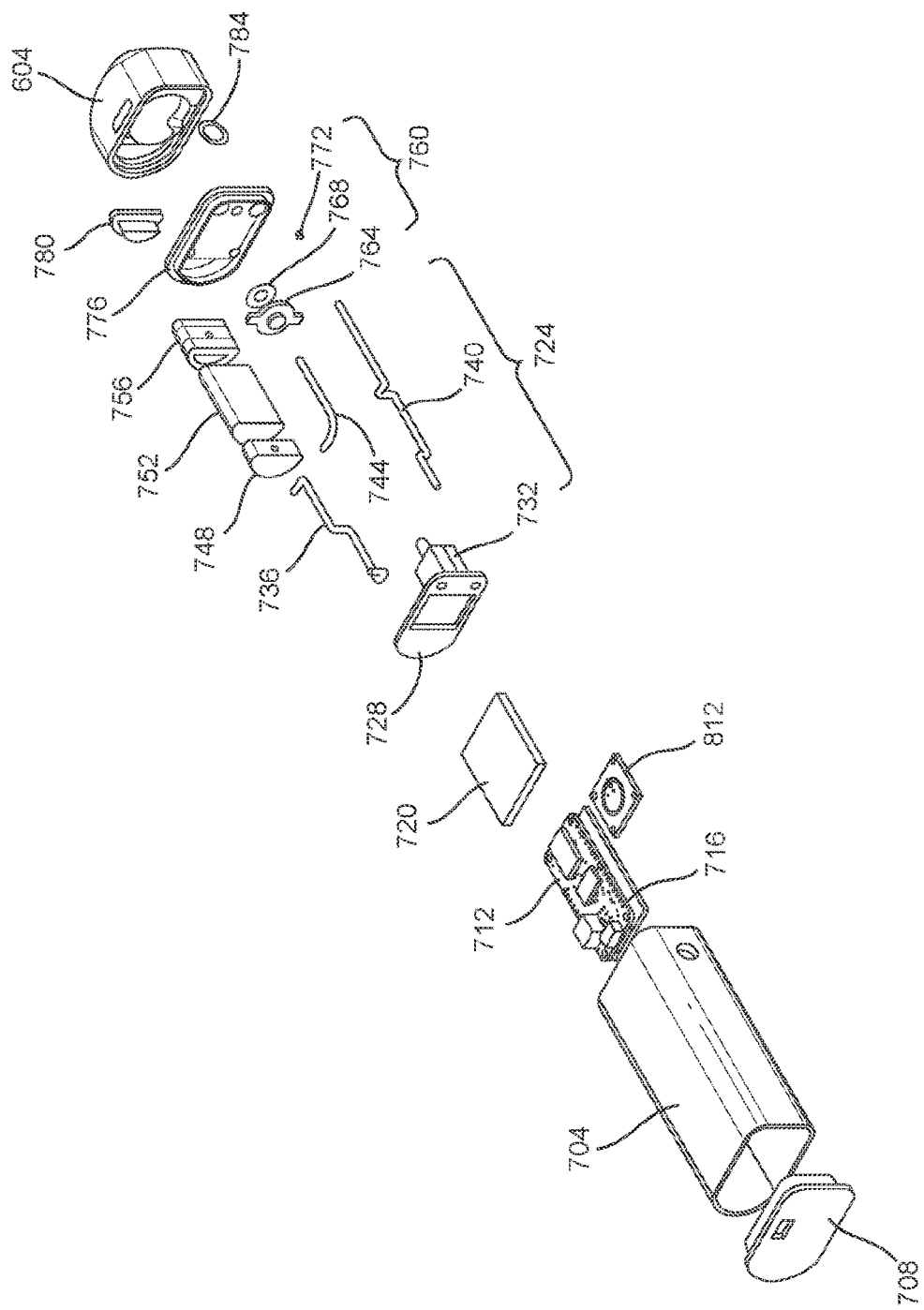
FIG. 7 is an exploded view of the portable inhalation device of FIG. 6 according to an embodiment of the present disclosure.

Referring to FIG. 7, an exploded view of the portable inhalation device 600 is shown according to an embodiment of the present disclosure. The portable inhalation device 600 includes a cover 704 of the body 608, to which an end cap 708 can be coupled. The portable inhalation device 600 includes a processing circuit 712. The processing circuit 712 can be similar to the processing circuit 170. The processing circuit 712 can include or be coupled with a driver 716. The driver 716 can control operation of an atomizer 760 (e.g., by controlling operation of flow controller 812 described further with reference to FIG. 8). The portable inhalation device 600 includes a power supply 720, which the processing circuit 712 can use to control operation of the atomizer 760.

For example, the driver 716 can take a 3V DC voltage from the power supply 720 and increase it to the appropriate range for use by the flow controller 812 or atomizer 760 (e.g., −50V to 50V).

The portable inhalation device 600 includes a support structure 724 that supports a medication cartridge 752. The support structure 724 can include a first base 728 coupled with a pressure sensor 732. A first tube 736 (e.g., channel) can connect the flow controller 812 with the medication cartridge 752. A second tube 740 (e.g., channel) can connect the pressure sensor 732 with the medication delivery component 604. A third tube 744 (e.g., channel) can connect the medication cartridge 752 with the atomizer 760. The tubes 736, 740, 744 can be shaped to couple the corresponding components while enabling a compact form factor for the portable inhalation device 600.

The support structure 724 can include a second base 748 which can be adjacent to the medication cartridge 752 between the medication cartridge 752 and the first base 728. A cartridge cover 756 can be adjacent to the medication cartridge 752 on an opposite side of the medication cartridge 752 from the second base 748, such as to function as a lid of the medication cartridge 752. In some embodiments, the portable inhalation device 600 includes a cap 780 which can couple with the cartridge cover 756 to seal the medication cartridge 752.

The portable inhalation device 600 includes an atomizer 760. The atomizer 760 can control flow of medication from the medication cartridge 752 into the medication delivery component 604. In some embodiments, the atomizer 760 includes a piezoelectric element 764, such as a piezoelectric disc, and a mesh 768. The atomizer 760 can include a magnet 772.

The portable inhalation device 600 can include a third base 776. The third base 776 can connect the atomizer 760 with the medication delivery component 604, such as to allow medication outputted from the atomizer 760 to flow into the medication delivery component 604. The third base 776 can connect the medication delivery component 604 with the pressure sensor 732 via the second tube 740.

In some embodiments, the portable inhalation device 600 includes a user interface element 784. The user interface element 784 can include at least one of user input device (e.g., button, switch) or a light (e.g., LED light). The user interface element 784 can receive a user input, such as a button press, and transmit the user input to the processing circuit 712, such as to receive instructions to turn on the portable inhalation device 600.

Figure 8:
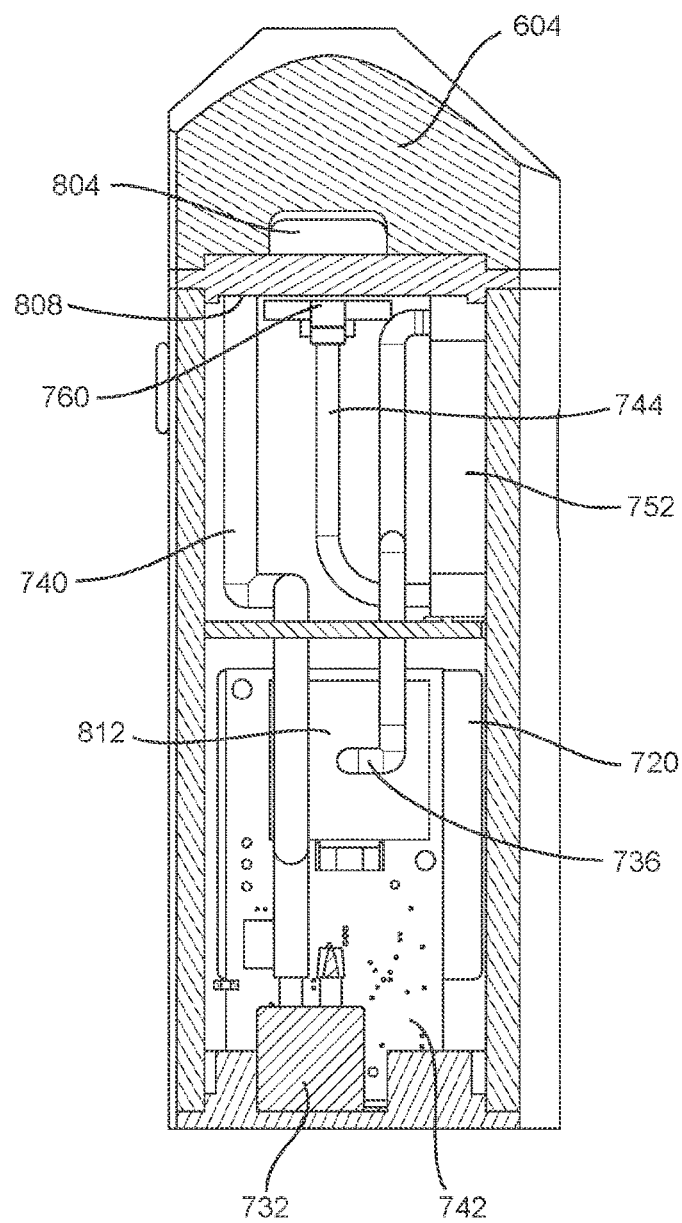
FIG. 8 is a section view of the portable inhalation device of FIG. 6 according to an embodiment of the present disclosure.

Referring to FIG. 8, a section view of the portable inhalation device 600 is shown according to an embodiment of the present disclosure. As shown in FIG. 8, the medication delivery component 604 defines a vent 804. The vent 804 can allow air driven through the medication delivery component 604 to exit via the vent 804, such as when a user blows into the medication delivery component 604.

The third base 776 can define a sensor opening 808. The sensor opening 808 fluidly couples the medication delivery component 604 with the second tube 740 and the pressure sensor 732. For example, changes in air pressure in the medication delivery component 604, such as when a user blows into the medication delivery component 604, can be detected by the pressure sensor 732 based on corresponding changes in air pressure in the second tube 740.

The portable inhalation device 600 can include a flow controller 812, such as a microblower. The flow controller 812 can be controlled by the driver 716. The flow controller 812 can apply pressure on air in the first tube 736 to drive the air to apply pressure on medication in the medication cartridge 752, so that the medication is driven out of the medication cartridge 752 into the third tube 744 and to the atomizer 760. The driver 716 can cause the atomizer 760 to transform the medication into a mist 912 for output via the medication delivery component 604.

Figure 9:
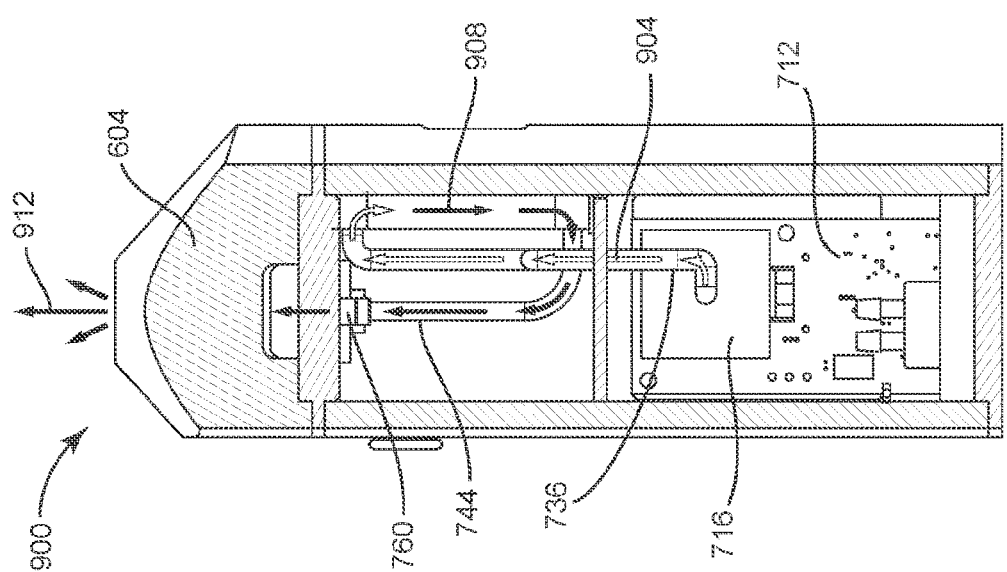
FIG. 9 is a section view of the portable inhalation device of FIG. 6 illustrating a medication delivery mode according to an embodiment of the present disclosure.

Referring now to FIG. 9, a section view of the portable inhalation device 600 is shown in which the portable inhalation device 600 is operating in a medication delivery mode 90 according to an embodiment of the present disclosure. In the medication delivery mode 900, the processing circuit 712 causes the flow controller 812 to drive air 904 into the medication cartridge 752. The resulting pressure applied by the air 904 on medication 908 in the medication cartridge 752 causes the medication 908 to flow through the third tube 744 and to the atomizer 760.

Figure 10:
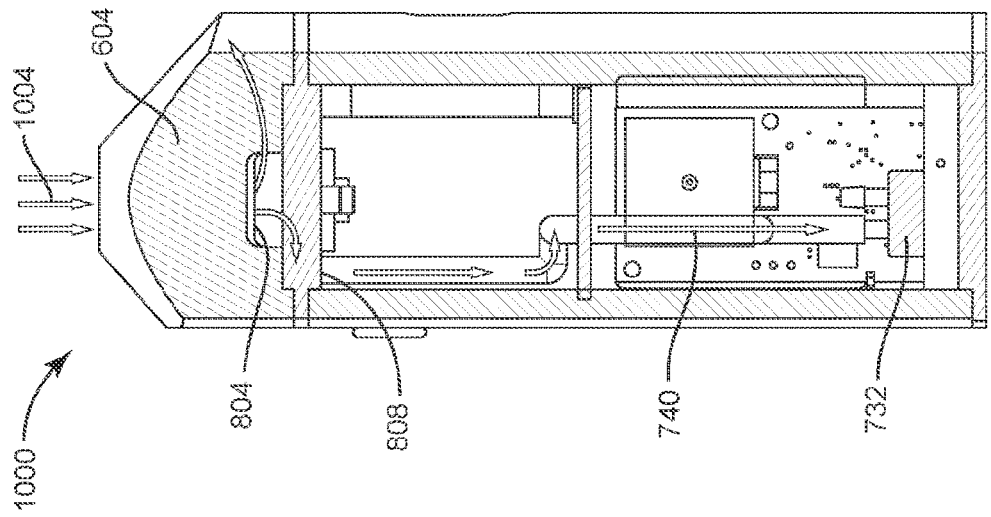
FIG. 10 is a section view of the portable inhalation device of FIG. 6 illustrating a measurement mode according to an embodiment of the present disclosure.

Referring now to FIG. 10, a section view of the portable inhalation device 600 is shown in which the portable inhalation device 600 is operating in a measurement mode 1000 according to an embodiment of the present disclosure. For example, air 1004 received from a user (e.g. blown by the user into the outlet opening 612) can flow through the medication delivery component 604 and into the second tube 740 via the sensor opening 808 to the pressure sensor 732, so that the pressure sensor 732 can detect pressure data regarding the air 1004 received from the user. Some of the air 1004 may exit the medication delivery component 604 via the vent 804.

Figure 11:
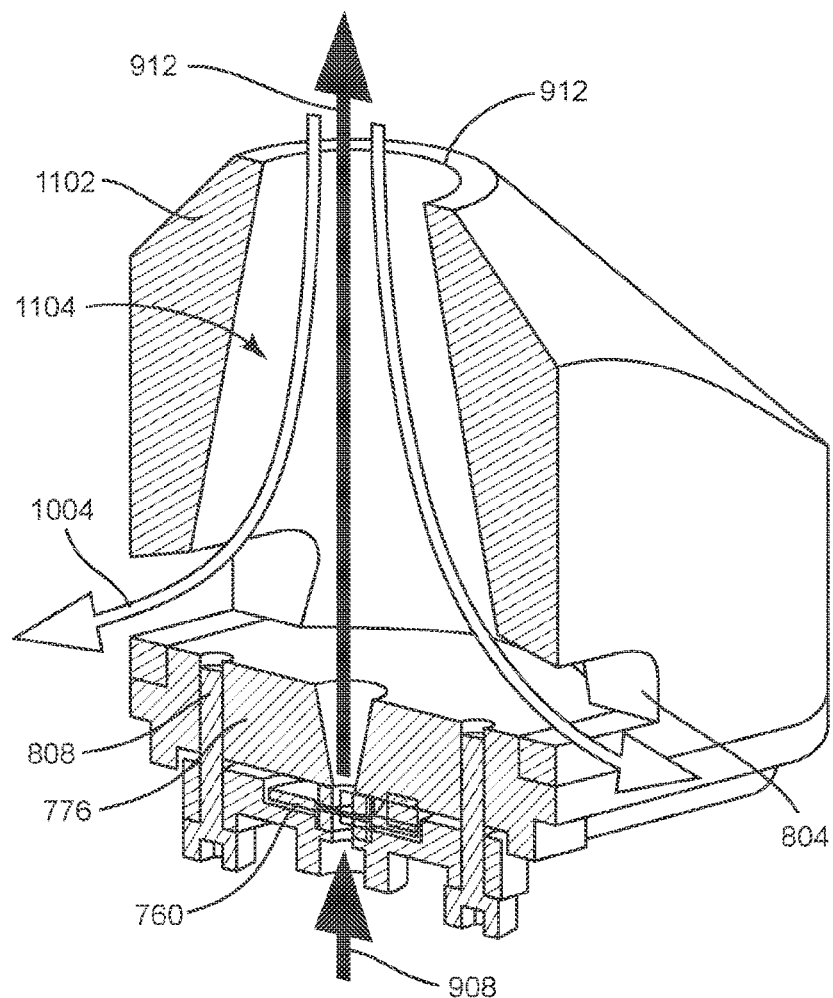
FIG. 11 is a detail view of a medication delivery component of the portable inhalation device of FIG. 6 according to an embodiment of the present disclosure.

Referring now to FIG. 11, a detail view of the medication delivery component 604 is shown according to an embodiment of the present disclosure. The medication delivery component 604 includes a diffuser 1104 extending between the outlet opening 612 and the third base 776. The diffuser 1104 can provide fluid communication between the outlet opening 612, the vent 804, the sensor opening 808, and the atomizer 760. The diffuser 1104 can define a diffuser surface 1104 extending from the outlet opening 612 to the vent 804. The diffuser surface 1104 can increase in diameter and/or cross-sectional area from the outlet opening 612 to the vent 804. For example, the diffuser surface 1104 can be a conical surface that increases in diameter from the outlet opening 612 to the vent 804, which can reduce pressure in the diffuser 1104 from the outlet opening 612 to the vent 804 (and the sensor opening 808 and atomizer 760).

Referring further to FIG. 7, the processing circuit 712 can be used to control operation of components of the portable inhalation device 600 to perform pulse-dose nebulization. For example, the processing circuit 712 can cause medication doses to be delivered during inhalation by a user, which can lower the dosage size required per treatment. For example, a typical albuterol ampule for nebulization may have 2.5 mg per mL; however, the present solution can perform pulse-dose nebulization to output doses of approximately 0.2 mg per treatment, increasing the lifespan of the medication cartridge 604 and the medication therein. For example, the processing circuit 712 can be used to perform pulse-dose nebulization by causing medication to be delivered responsive to detecting inhalation, such as delivering the medication only during inhalation, allowing the medication cartridge 604 to carry multiple doses (e.g., five doses), and therefore mitigating the need to replace the medication cartridge 604 following each treatment. In some embodiments, the medication cartridge 604 stores a treatment for chronic obstructive pulmonary disease (COPD), such as a treatment of albuterol and ipratropium bromide (e.g., DUONEB). COPD exacerbations may often result in hospitalization; by using pulse-dose nebulization, the processing circuit 712 can reduce the volume or medication needed to be delivered to the user, reducing the likelihood that the user does not have access to sufficient medication when a COPD exacerbation occurs.

Referring to FIG. 12, the processing circuit 712 can use pressure data received from the pressure sensor 732 to perform spirometry measurements. For example, the processing circuit 712 can convert received pressure data to volume data (e.g., volumetric flow), such as based on a calibration function as described above. The processing circuit 712 can calculate a measurement 1204, such as volume as a function of time. Based on the measurement 1204, the processing circuit 712 can calculate parameters such as forced expiratory volume (FEV) in one second (FEV1) 1208. FEV1 can represent the volume blown into the portable inhalation device 600 from a first point in time at which the processing circuit 712 detects air being blown into the portable inhalation device 600 based on the pressure data to one second after the first point in time. The processing circuit 712 can calculate forced vital capacity (FVC) 1212 as a total amount of air blown into the portable inhalation device 600 (e.g., beginning from the first point in time). The processing circuit 712 can calculate a ratio of FEV1 to FVC. The processing circuit 712 can use the FEV1 data to more precisely monitor the user's breathing (e.g., compared to peak flow, which may depend on effort expended by the user), such as to correlate the FEV1 data with other parameters regarding subject health, such as to generate a correlation enabling the FEV1 to be used as a predictor of subject health.

The processing circuit 712 can use the volume data to generate a flow volume loop 1216 indicating flow rate (e.g., L/s) as a function of volume (e.g., L). For example, the processing circuit 712 can identify expiration 1220 and inspiration 1224 by the user. The processing circuit 712 can calculate parameters such as peak expiratory flow (PEF), maximal mid-expiratory flow (MEF), forced expiratory flow (FEF) at various milestones (e.g., $FEF_{25\%}$ indicating 25 percent of total expired volume, $FEF_{50\%}$ indicating 50 percent of total expired volume; $FEF_{75\%}$ indicating 75 percent of total expired volume), and forced inspiratory flow at various milestones (e.g., $FiF_{25\%}$ indicating 25 percent of total inspired volume; $FIF_{50\%}$ indicating 50 percent of total inspired volume; $FIF_{75\%}$ indicating 75 percent of total inspired volume). The processing circuit 712 can maintain a database of this information for the user, such as to enable longitudinal analysis regarding the spirometry data.

The processing circuit 712 can generate a chart 1228 comparing the spirometry data to various other variables. For example, the processing circuit 712 can generate the chart 1228 to compare peak flow 1232 to an air quality index (AQI) parameter 1236. The processing circuit 712 can receive the AQI parameter data from a remote source (e.g., via communication electronics as described with reference to the processing circuit 170). The processing circuit 712 can receive parameter data regarding parameters such as pollution, temperature, humidity, pollen index, and location, and execute a correlation to determine a relationship between the parameter(s) and the spirometry data.

Referring to FIG. 13, a subject monitoring system 1300 is shown according to an embodiment of the present disclosure. The subject monitoring system 1300 can include a portable inhalation device 1304 (e.g., the portable inhalation device 100, the portable inhalation device 600) and a remote electronic device 1308. The remote electronic device 1308 can be a portable electronic device, or a server that communicates with the portable inhalation device 1304 (which may include using a portable electronic device as an intermediary between the portable inhalation device 1304 and the remote electronic device 1308). The remote electronic device 1308 can include a processing circuit 1312, a user interface 1316, and a communications circuit 1320. The processing circuit 1312 can be similar to and performs functions described with reference to the processing circuits 170, 712, such as to calculate volume data based on pressure data and compare the volume data to parameters such as pollution, temperature, humidity, pollen index, and location (e.g., received by the communications circuit 1320 via a remote data source 1324, such as the Internet). The user interface 1316 can receive user input and present information regarding operation of the subject monitoring system 1300. The user interface 1300 may include one or more user input devices, such as buttons, dials, sliders, or keys, to receive input from a user. The user interface 1300 may include one or more display devices (e.g., OLED. LED, LCD, CRT displays), speakers, tactile feedback devices, or other output devices to provide information to a user. The communications circuit 1320 can include wired or wireless interfaces (e.g., jacks, antennas, transmitters, receivers, transceivers, wire terminals, etc.) for conducting data communications with various systems, devices, or networks. For example, the communications circuit 1320 can include an Ethernet card and port for sending and receiving data via an Ethernet-based communications network. The communications circuit 1320 can include a WiFi transceiver for communicating via a wireless communications network. The communications circuit 1320 can communicate via local area networks (e.g., a building LAN), wide area networks (e.g., the Internet, a cellular network), and/or conduct direct communications (e.g., NFC. Bluetooth). In some embodiments, the communications circuit 1320 can conduct wired and/or wireless communications. For example, the communications circuit 1320 can include one or more wireless transceivers (e.g., a Wi-Fi transceiver, a Bluetooth transceiver, a NFC transceiver, a cellular transceiver). In some embodiments, the remote electronic device 1308 includes a position sensor 1332 (e.g., GPS sensor, accelerometer), which can provide position data to the processing circuit 1312 that the processing circuit 1312 can correlate with data received from the portable inhalation device 1304.

The processing circuit 1312 can maintain a user database 1328. The user database 1328 can include data captured by the portable inhalation device 1304, such as inspiration and expiration data, such as described with reference to calculations performed by the processing circuit 712. The user database 1328 can store dosage information for the user. The user database 1328 can store location data received from the position sensor 1332, and the processing circuit 1312 can map the location data to other data (e.g., based on when the other data was detected).

Figure 12:
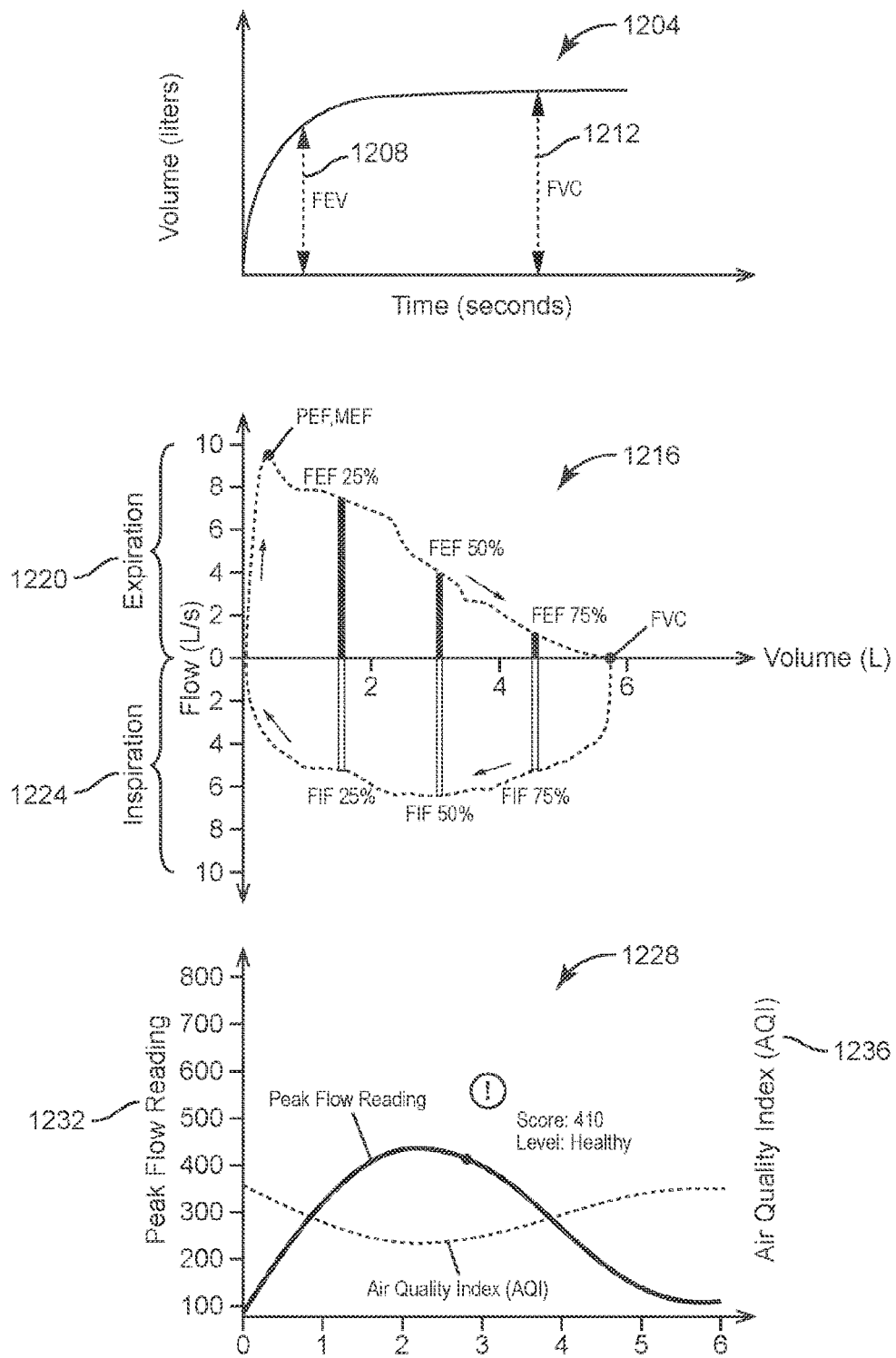
FIG. 12 depicts charts that can be generated using pressure data detected by the portable inhalation device of FIG. 6 according to an embodiment of the present disclosure.
Figure 13:
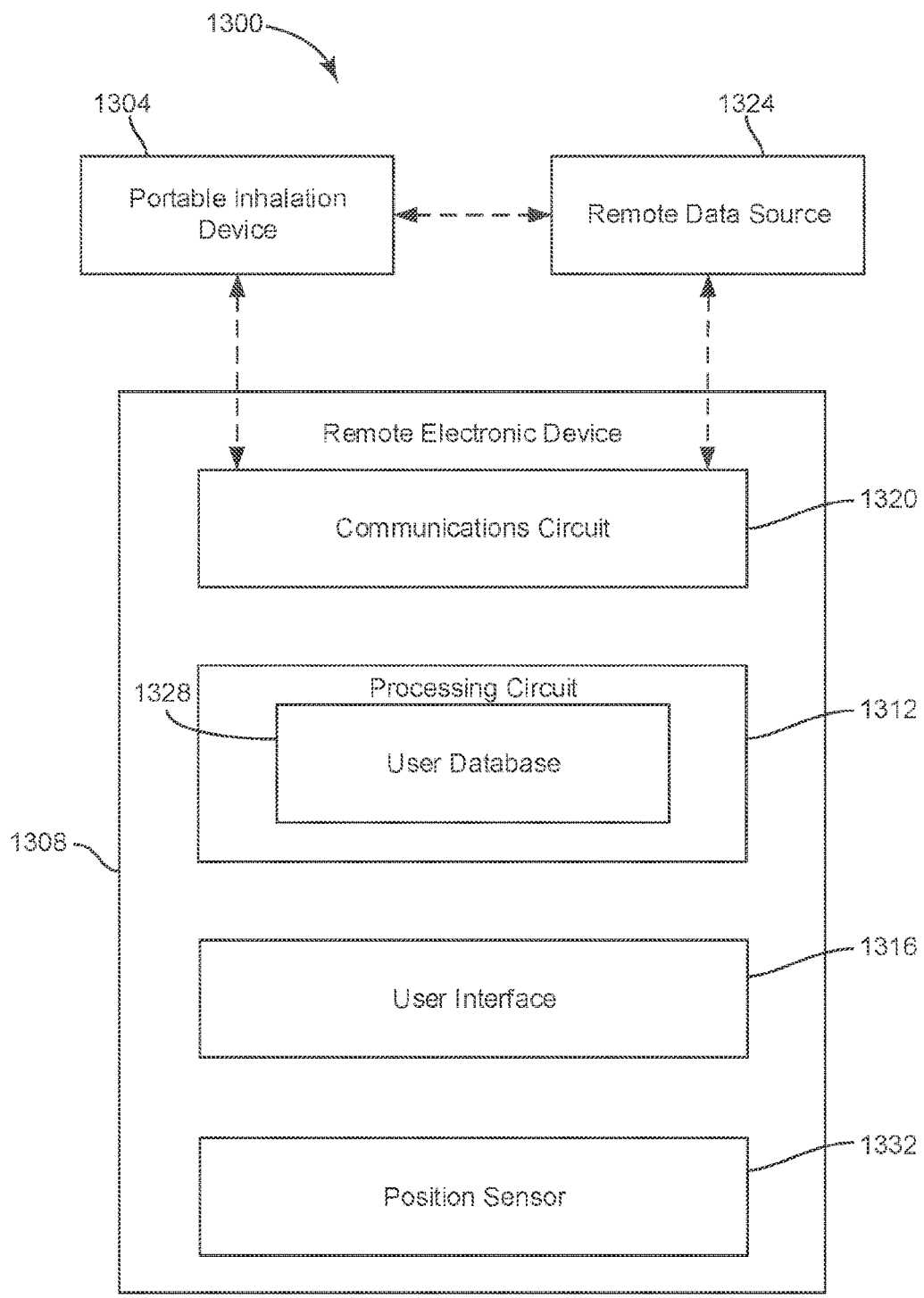
FIG. 13 is a block diagram of a subject monitoring system that can use various portable inhalation devices described herein according to an embodiment of the present disclosure.
Figure 14A:
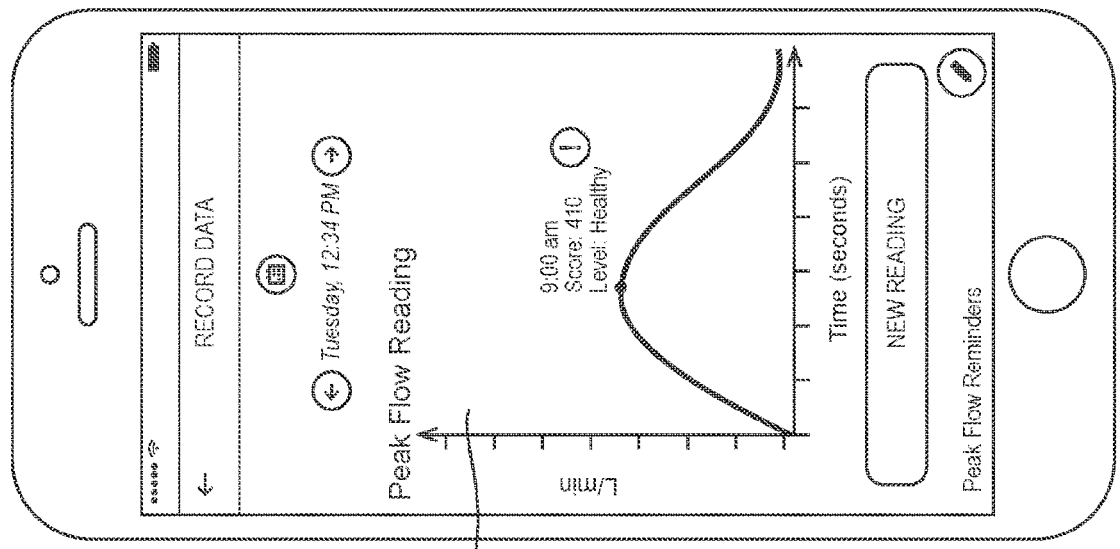
FIGS. 14A and 14B depict user interfaces that can be presented using the subject monitoring system of FIG. 13 according to an embodiment of the present disclosure.
Figure 14A:
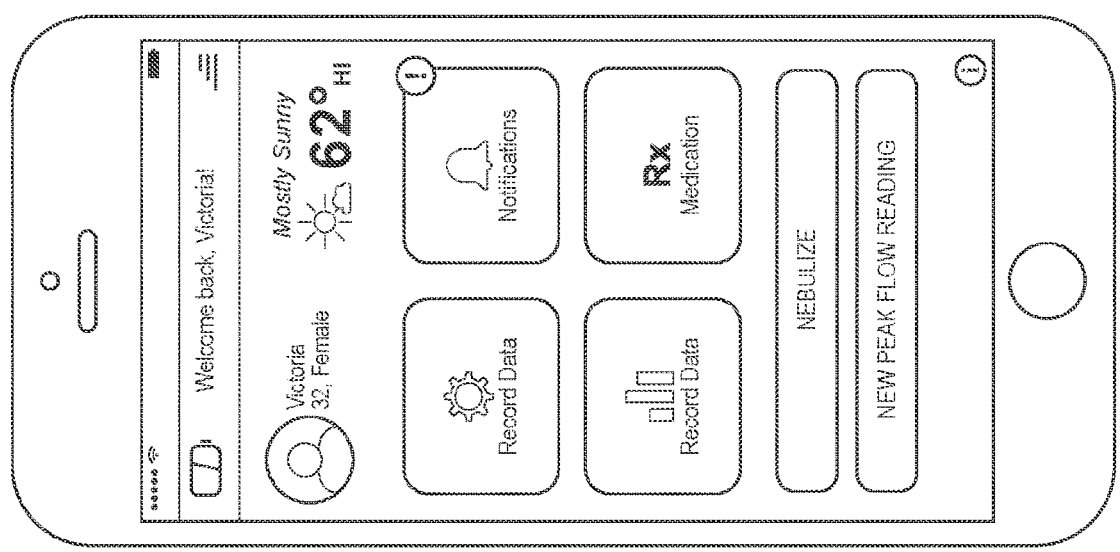
Figure 14B:
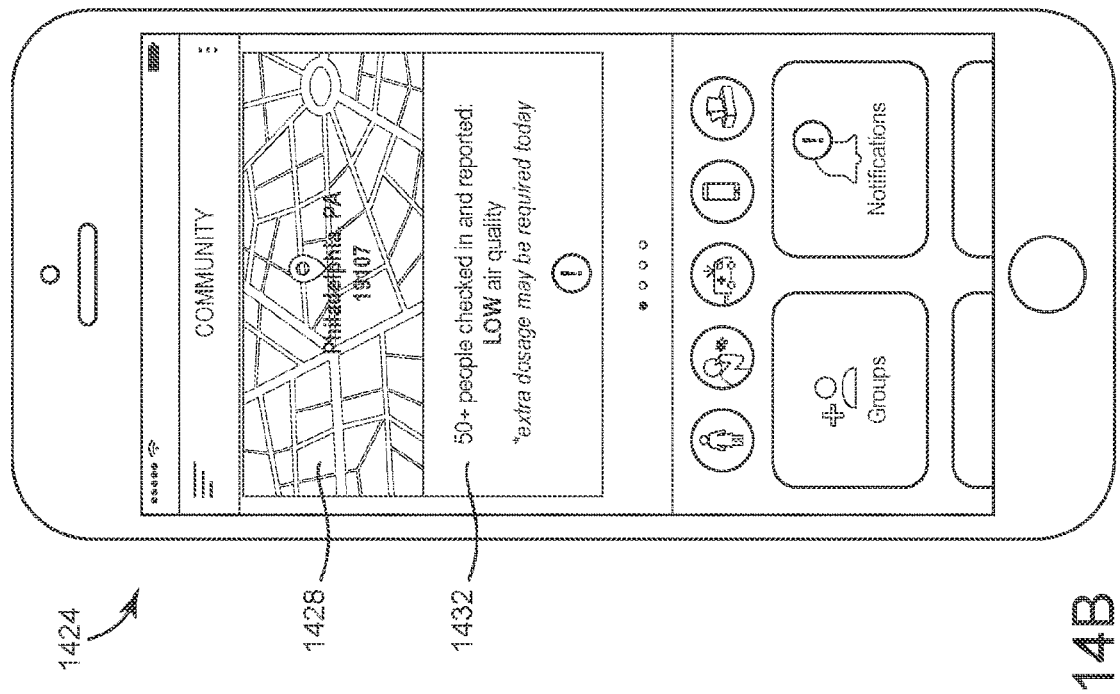
Figure 14B:
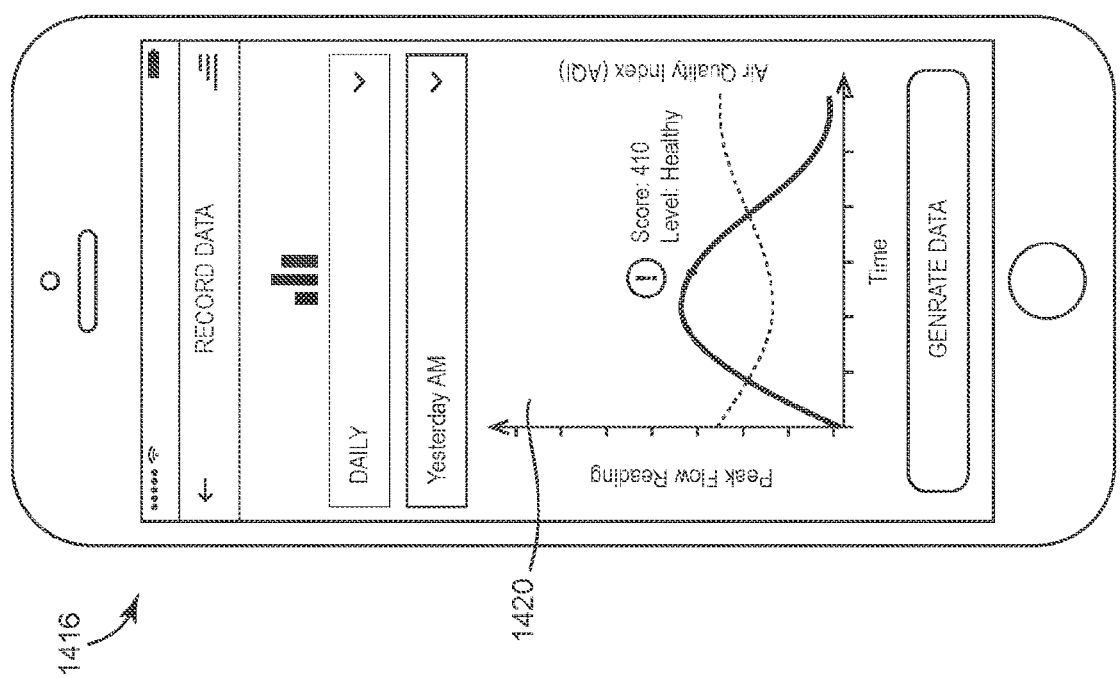

The remote electronic device 1308 can generate various outputs for presentation via the user interface 1316. For example, referring to FIGS. 14A and 14B, the remote electronic device 1308 can present a first interface 1404 that can include user data, such as name, age, and gender, as well as remote source data, including environmental data such as weather data and air quality data. The remote electronic device 1308 can present a second interface 1408, which can include spirometry data, such as a peak flow chart 1412. The remote electronic device 1308 can generate the peak flow chart 1412 based on information received from the portable inhalation device 1304 and/or information maintained in the user database 1328. The remote electronic device 1308 can present a third interface 1416, which can include spirometry data, such as the chart 1228 described with reference to FIG. 12. The remote electronic device 1308 can present a fourth interface 1420, which can include location-based data, such as an indication of air quality 1428 in a particular location. As shown in FIG. 14, the processing circuit 1312 can calculate a recommended dosage based on the air quality and generate the fourth interface 1420 to include a recommendation 1432 regarding the recommended dosage. The processing circuit 1312 can determine a relationship between the spirometry data and the environmental data, such as to generate the third interface 1416.

Figure 15:
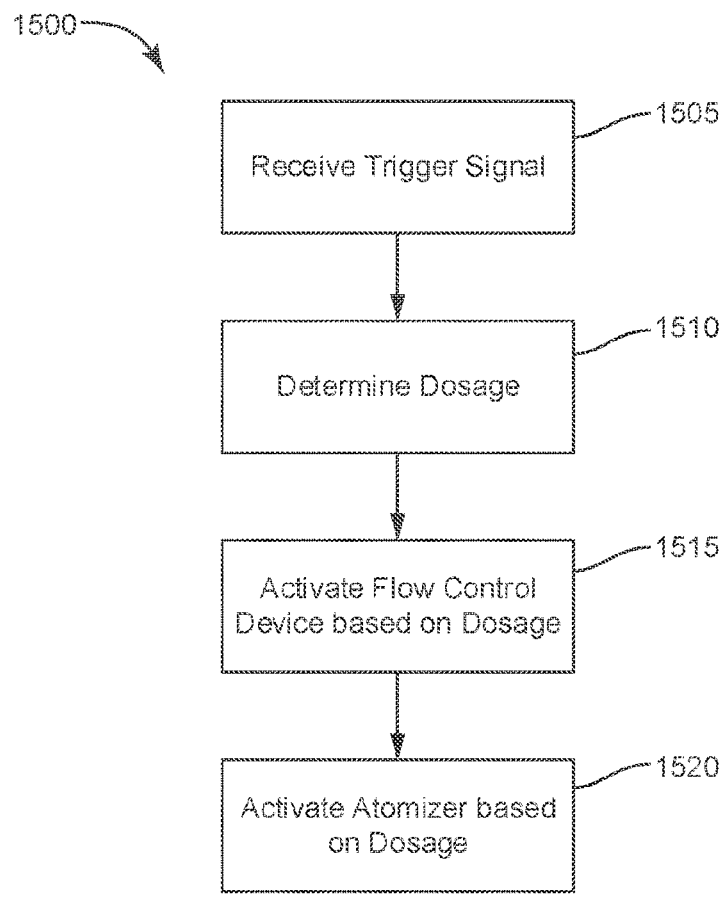
FIG. 15 is a flow diagram of a method of delivering medication using a portable inhalation device according to an embodiment of the present disclosure.

Referring to FIG. 15, a method 1500 of operating a portable inhalation device is shown according to an embodiment of the present disclosure. The method 1500 may be performed by the portable inhalation device 100 described with reference to FIGS. 1-5C and/or the portable inhalation device 600 described with reference to FIGS. 6-14. Computational processes executed as part of the method 1500 may be performed by a remote device (e.g., portable electronic device, remote server).

At 1505, a trigger signal is received (or generated). The trigger signal can be received based on a pressure signal indicating an inhalation being performed on a medication delivery component of the portable inhalation device. For example, a pressure value indicated by the pressure signal can be compared to a trigger threshold associated with inhalation, and if the pressure value is greater than the trigger threshold, the trigger signal can be received (or generated). In some embodiments, the trigger signal is received based on a user input. In some embodiments, the trigger signal is received as a control signal from a remote device.

At 1510, a dosage of medication is determined. The dosage may be determined by retrieving the dosage from a lookup table in a user database. The dosage may be determined based on breathing/spirometry characteristics of a user determined based on pressure data. In some embodiments, the user database includes a maximum dosage, which may not be if the pressure data would otherwise map to a dosage higher than the maximum dosage.

At 1515, a flow controller of the portable inhalation device is activated based on the determined dosage. The flow controller can be activated for a first duration of time corresponding to the dosage. The duration of time may correspond to a pressure applied by the flow controller on the medication or a flow rate of air flowing from the flow controller into a medication storage component of the portable inhalation device.

At 1520, an atomizer of the portable inhalation device is activated based on the dosage. Activating the atomizer may include generating droplets from the medication and/or increasing a velocity of the medication in a direction towards an outlet opening of the portable inhalation device. The atomizer may be activated for a second duration of time corresponding to the dosage. The second duration of time may correspond to a time sufficient to generate droplets of the dosage of medication mid/or dispense the dosage of medication through the atomizer towards the outlet opening. The atomizer may be activated after a first time delay subsequent to activation of the flow controller until deactivation at expiration of the second duration of time. The first time delay may correspond to a time required by the dosage of medication to flow from the medication storage component to the atomizer. Activating the atomizer can cause the medication to be delivered through the outlet opening to a patient.

In some embodiments, the portable inhalation device is configured to collect and/or track airway measurement data before, during and/or after treatment. In some embodiments, the portable inhalation device can include a short communication module, such as Bluetooth, that is configured to receive airway measurement data before, during, and after treatment.

In some embodiments, the portable inhalation device can include an integrated pulse oximeter to collect blood oxygen levels. The integrated pulse oximeter can be sized and configured on the portable inhalation device such that the pulse oximeter can determine a blood oxygen level of a user while the user is holding the portable inhalation device. The portable inhalation device can be configured to collect both the airway measurement data with blood oxygen levels to determine a correlation between a status of an airway and blood oxygen levels. In some embodiments, the portable inhalation device can be configured to receive or obtain measurements throughout the day and these measurements will be linked to other specific variables at that moment in time such as geographic location (urban vs rural), allergy maps, air quality, pollen counts, and weather. In some embodiments, the portable inhalation device can include a location sensor, such as a GPS, to determine a current location of the portable inhalation device. Using the location obtained from the location sensor, values for specific variables for that location can be determined. The storage of this data over time will provide valuable predictive insight into the individual's asthma state (e.g., the asthma is worse during times when the pollen counts are over a certain level or the humidity is over a certain percentage). The data can be evaluated with specific proprietary algorithms and calculations. This information can provide actionable information that allows for informed health care decisions by their health care provider.

In some embodiments, the portable inhalation device can include a removable cartridge that stores medication. The portable inhalation device can include a fluid pathway from a location proximal to where the removable cartridge is inserted within the portable inhalation device and the piezoelectric device. With the use of a cartridge, there is less of a barrier to use and improved compliance as it is easier and less effort to start the nebulization process. The cartridge housing will have tactile haptic feedback on placement and removal to further simplify the experience.

What is claimed is:

1. A method for performing spirometry, comprising:
   receiving, by one or more processors, for a first point in time and a second point in time, pressure data from a pressure sensor of a portable inhalation device, the pressure data associated with at least one of inhalation by a user of the portable inhalation device or exhalation by the user, the pressure sensor coupled with a tube extending through the portable inhalation device from an opening of the portable inhalation device to the pressure sensor;
   determining, by the one or more processors, for the first point in time and the second point in time, volume data corresponding to a breathing characteristic of the user, based on the pressure data;
   identifying, by the one or more processors, for the first point in time and the second point in time, one or more parameters including at least one of pollution, temperature, humidity, pollen index, or location;
   determining, by the one or more processors, for the first point in time and the second point in time, a respiratory condition of the user based on the breathing characteristic of the user;
   determining, by the one or more processors, for the first point in time, a dosage of medication to be delivered to the user in response to identifying the respiratory condition of the user for the first point in time;
   updating, by the one or more processors, for the second point in time, an updated value of the dosage of medication based on the respiratory condition for the second point in time, to provide dynamic updating of the dosage; and
   outputting, by the one or more processors, a user interface element comprising the volume data and comprising the one or more parameters, for the first point in time and the second point in time, to represent a relationship between the volume data and the one or more parameters.

2. The method of claim 1, comprising generating the pressure data during a measurement mode of the portable inhalation device.

3. The method of claim 1, wherein the volume data comprises a flow rate.

4. The method of claim 3, wherein the flow rate comprises at least one of a forced expiratory volume or a peak expiratory flow.

5. The method of claim 1, wherein determining a relationship between the volume data with the parameter comprises comparing the indication of volume with an air quality index parameter.

6. The method of claim 1, further comprising maintaining, by the one or more processors, longitudinal data corresponding to the volume data and the parameter.

7. The method of claim 1, further comprising:
   determining, by the one or more processors, the dosage of medication based on user data stored in a user database, the user database mapping one or more users to predetermined dosages.

8. The method of claim 1, further comprising determining the volume data, for each of the first point in time and the second point in time, to include a forced expiratory volume (FEV1).

9. A system, comprising:
   a portable inhalation device comprising a pressure sensor to detect pressure data, for a first point in time and a second point in time, associated with at least one of inhalation by a user of the portable inhalation device or exhalation by the user, the pressure sensor coupled with a tube extending through the portable inhalation device from an opening of the portable inhalation device to the pressure sensor, and
   one or more processors configured to:
      determine volume data, for the first point in time and the second point in time, based on the pressure data;
      identify, for the first point in time and the second point in time, one or more parameters including at least one of pollution, temperature, humidity, pollen index, or location;
      determine a dosage of medication to be delivered to the user based on a breathing characteristic of the user represented by the volume data for the first point in time;
      update the dosage of medication based on a breathing characteristic of the user represented by the volume data for the second point in time, to allow for dynamic updating of the dosage of medication; and cause presentation of a user interface comprising the volume data and the one or more parameters, during the period of time, to represent a relationship between the volume data and the one or more parameters.

10. The system of claim 9, wherein the one or more processors are configured to receive the pressure data during a measurement mode of the portable inhalation device.

11. The system of claim 9, wherein the volume data comprises a flow rate.

12. The system of claim 11, wherein the flow rate comprises at least one of a forced expiratory volume or a peak expiratory flow.

13. The system of claim 9, wherein the one or more processors are configured to relate the volume data with the parameter by comparing the volume data with an air quality index parameter.

14. The system of claim 9, wherein the one or more processors are configured to maintain longitudinal data corresponding to the volume data and the parameter.

15. The system of claim 9, wherein an electronic device remote from the portable inhalation device comprises the one or more processors.

16. The system of claim 9, wherein the portable inhalation device comprises an atomizer to provide medication to the user.

17. A non-transitory processor-readable medium comprising processor-readable instructions that when executed by one or more processors, cause the one or more processors to:
receive, from a pressure sensor of a portable inhalation device, pressure data associated with at least one of inhalation by a user of the portable inhalation device or exhalation by the user, the pressure sensor coupled with a tube extending through the portable inhalation device from an opening of the portable inhalation device to the pressure sensor;
determine flow rate data associated with a flow rate of the at least one of the inhalation or the exhalation, the flow rate data corresponding to a breathing characteristic of the user, for a first point in time of a first use cycle of the portable inhalation device and a second point in time of a second use cycle of the portable inhalation device, based on the pressure data;
identify, for the first point in time and the second point in time, one or more parameters including at least one of pollution, temperature, humidity, pollen index, or location;
determine, for the first point in time and the second point in time, a respiratory condition of the user based on the breathing characteristic of the user; and
determine a dosage of medication to deliver to the user for the first point in time based on the respiratory condition determined for the first point in time;
update the dosage based on the respiratory condition determined for the second point in time; and
deliver the updated dosage of medication to the user during the second use cycle.

18. The non-transitory processor-readable medium of claim 17, wherein the flow rate data comprises at least one of a forced expiratory volume or a peak expiratory flow.

19. The non-transitory processor-readable medium of claim 17, further comprising instructions to cause the one or more processors to maintain longitudinal data corresponding to the flow rate data and the parameter.

\* \* \* \* \*